US009968456B2

(12) United States Patent
Song

(10) Patent No.: US 9,968,456 B2
(45) Date of Patent: May 15, 2018

(54) CUSTOMIZED ACETABULAR CUP POSITIONING GUIDE AND METHOD OF GENERATING AND EMPLOYING SUCH A GUIDE

(71) Applicant: Howmedica Osteonics Corporation, Mahwah, NJ (US)

(72) Inventor: Keun Song, Palo Alto, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days. days.

(21) Appl. No.: 15/178,065

(22) Filed: Jun. 9, 2016

(65) Prior Publication Data

US 2016/0278926 A1 Sep. 29, 2016

Related U.S. Application Data

(62) Division of application No. 13/960,498, filed on Aug. 6, 2013.
(Continued)

(51) Int. Cl.
*A61B 17/58* (2006.01)
*A61B 17/60* (2006.01)
(Continued)

(52) U.S. Cl.
CPC ........ *A61F 2/30942* (2013.01); *A61F 2/4609* (2013.01); *A61F 2002/30948* (2013.01);
(Continued)

(58) Field of Classification Search
None
See application file for complete search history.

(56) References Cited

U.S. PATENT DOCUMENTS 5,133,758 A 7/1992 Hollister
5,150,304 A 9/1992 Berchem
(Continued)

FOREIGN PATENT DOCUMENTS

WO WO 2009/134620 A2 11/2009
WO WO 2010/124164 A1 10/2010
(Continued)

OTHER PUBLICATIONS

International Search Report and Written Opinion, PCT/US2011/040869, dated Aug. 22, 2011.
(Continued)

*Primary Examiner* — Sameh Boles
(74) *Attorney, Agent, or Firm* — Polsinelli PC

(57) ABSTRACT

Implementations described and claimed herein provide an arthroplasty system and methods for positioning an acetabular cup implant. In one implementation, the system includes a shape-match hip guide having a patient specific mating region that is a negative of the surface contour of the inside surface of the patient's acetabular cup, and a directional rod that extends generally along the axis of the patient's femoral head and femoral neck. They system can additionally include an outrigger or silo device to aid in the alignment of surgical tools for preparing and implanting of the prosthetic acetabular cup in the patient's acetabular cup. Related methods are also disclosed herein for generating a shape-match guide and implanting an acetabular cup with the guide.

21 Claims, 45 Drawing Sheets

Related U.S. Application Data

(60) Provisional application No. 61/794,662, filed on Mar. 15, 2013.

(51) Int. Cl.
    *A61F 2/00*         (2006.01)
    *A61F 2/30*         (2006.01)
    *A61F 2/46*         (2006.01)

(52) U.S. Cl.
    CPC .............. *A61F 2002/30952* (2013.01); *A61F 2002/4681* (2013.01); *A61F 2002/4687* (2013.01); *Y10T 29/49002* (2015.01)

(56) References Cited

U.S. PATENT DOCUMENTS

| | | |
|---|---|---|
| 5,364,403 A | 11/1994 | Peterson et al. |
| 5,417,694 A | 5/1995 | Marik |
| 5,454,717 A | 10/1995 | Andreiko |
| 5,520,694 A | 5/1996 | Dance et al. |
| 5,611,353 A | 3/1997 | Dance et al. |
| 5,735,856 A | 4/1998 | McCue |
| 5,769,856 A | 6/1998 | Dong et al. |
| 6,395,005 B1 | 5/2002 | Lovell |
| 6,676,706 B1 | 1/2004 | Mears et al. |
| 6,757,582 B2 | 6/2004 | Brisson et al. |
| 6,935,480 B2 | 8/2005 | Ziemer |
| 6,991,656 B2 | 1/2006 | Mears |
| 7,584,080 B2 | 9/2009 | Taylor et al. |
| 7,651,501 B2 | 1/2010 | Penenberg |
| 7,927,338 B2 | 4/2011 | Laffargue et al. |
| 7,931,652 B2 | 4/2011 | Ferrante et al. |
| 8,535,387 B2 | 9/2013 | Meridew et al. |
| 9,014,438 B2 | 4/2015 | Habets |
| 9,265,509 B2 | 2/2016 | Park et al. |
| 9,717,509 B2 | 8/2017 | Bono et al. |
| 2002/0055679 A1 | 5/2002 | Sati |
| 2002/0183760 A1 | 12/2002 | McGovern |
| 2005/0065617 A1 | 3/2005 | Moctezuma de la Barrera et al. |
| 2006/0093240 A1 | 5/2006 | Sabuncu et al. |
| 2007/0038223 A1 | 2/2007 | Marquart |
| 2007/0270680 A1 | 11/2007 | Sheffer |
| 2008/0009952 A1 | 1/2008 | Hodge |
| 2008/0208081 A1 | 8/2008 | Murphy |
| 2008/0269757 A1 | 10/2008 | McMinn |
| 2009/0089026 A1 | 4/2009 | Rodriguez Y Baena |
| 2009/0149965 A1 | 6/2009 | Quaid |
| 2009/0192620 A1 | 7/2009 | Ebbitt |
| 2009/0264894 A1 | 10/2009 | Wasielewski |
| 2010/0016984 A1 | 1/2010 | Trabish |
| 2010/0036252 A1 | 2/2010 | Chalana et al. |
| 2010/0286700 A1 | 11/2010 | Snider et al. |
| 2011/0009868 A1 | 1/2011 | Sato |
| 2011/0015637 A1 | 1/2011 | De Smedt et al. |
| 2011/0015639 A1 | 1/2011 | Metzger et al. |
| 2011/0024583 A1 | 2/2011 | Hoernig |
| 2011/0093086 A1 | 4/2011 | Witt et al. |
| 2011/0184419 A1 | 7/2011 | Meridew et al. |
| 2011/0224674 A1 | 9/2011 | White et al. |
| 2011/0306978 A1 | 12/2011 | Ries et al. |
| 2011/0313424 A1 | 12/2011 | Bono et al. |
| 2012/0041445 A1 | 2/2012 | Roose et al. |
| 2012/0109137 A1 | 5/2012 | Iannotti et al. |
| 2012/0109138 A1 | 5/2012 | Meridew et al. |
| 2012/0123423 A1 | 5/2012 | Fryman |
| 2012/0141034 A1 | 6/2012 | Iannotti et al. |
| 2012/0143267 A1 | 6/2012 | Iannotti et al. |
| 2012/0172884 A1 | 7/2012 | Zheng et al. |
| 2012/0226283 A1 | 9/2012 | Meridew et al. |
| 2012/0265208 A1 | 10/2012 | Smith |
| 2013/0144392 A1 | 6/2013 | Hughes |
| 2013/0211792 A1 | 8/2013 | Kang |
| 2013/0297265 A1 | 11/2013 | Baloch |
| 2014/0013565 A1 | 1/2014 | MacDonald et al. |
| 2014/0046342 A1 | 2/2014 | Hellier |
| 2014/0189508 A1 | 7/2014 | Granchi |
| 2014/0270423 A1 | 9/2014 | Zellner |
| 2014/0276240 A1 | 9/2014 | Stein |
| 2014/0276870 A1* | 9/2014 | Eash .................. A61B 17/1746 606/91 |
| 2014/0282194 A1 | 9/2014 | Nikou |
| 2014/0303990 A1 | 10/2014 | Schoenefeld |
| 2014/0324061 A1 | 10/2014 | Gotte |
| 2014/0343557 A1 | 11/2014 | Mueller |
| 2014/0350389 A1 | 11/2014 | Powell |
| 2016/0015466 A1 | 1/2016 | Park et al. |
| 2016/0070436 A1 | 3/2016 | Thomas |
| 2016/0074048 A1 | 3/2016 | Pavlovskaia et al. |
| 2016/0095609 A1 | 4/2016 | Park et al. |
| 2016/0213491 A1 | 7/2016 | Schoenefeld |
| 2016/0228194 A1 | 8/2016 | Park et al. |
| 2016/0228195 A1 | 8/2016 | Park et al. |
| 2016/0228196 A1 | 8/2016 | Park et al. |
| 2016/0228197 A1 | 8/2016 | Park et al. |
| 2016/0302806 A1 | 10/2016 | Song |

FOREIGN PATENT DOCUMENTS

| | | |
|---|---|---|
| WO | WO 2011/080260 A1 | 7/2011 |
| WO | WO 2013/013170 A1 | 1/2013 |

OTHER PUBLICATIONS

Taylor et al., "Computer-integrated revision total hip replacement surgery: concept and preliminary results," Medical Image Analysis (1999) vol. 3, No. 3, pp. 301-319.
Amendment Under 37 CFR 1.312, U.S. Appl. No. 14/824,731, dated Dec. 28, 2015.
Canadian Office Action, CA2642616, dated Feb. 26, 2016.
Canadian Office Action, CA2708393, dated Mar. 11, 2016.
Canadian Office Action, CA2721762, dated Nov. 10, 2015.
Canadian Office Action, CA2721762, dated Jul. 20, 2016.
Decision on Appeal, U.S. Appl. No. 12/391,008, dated Dec. 11, 2015.
EP Communication pursuant to Article 94(3) EPC, EP10192631.9, dated Feb. 12, 2016.
EP Search Report and Opinion, EP09800841.0, dated Mar. 22, 2016.
Final Office Action, U.S. Appl. No. 11/946,002, dated Nov. 30, 2015.
Final Office Action, U.S. Appl. No. 13/923,093, dated Jul. 14, 2016.
Final Office Action, U.S. Appl. No. 14/011,998, dated Jul. 14, 2016.
Final Office Action, U.S. Appl. No. 14/084,255, dated Jul. 26, 2016.
Final Rejection, U.S. Appl. No. 13/749,095, dated Dec. 24, 2015.
Final Rejection, U.S. Appl. No. 14/476,500, dated Feb. 1, 2016.
Non-Final Office Action, U.S. Appl. No. 11/946,002, dated May 18, 2016.
Non-Final Office Action, U.S. Appl. No. 13/923,093, dated Dec. 2, 2015.
Non-Final Office Action, U.S. Appl. No. 14/011,998, dated Feb. 12, 2016.
Non-Final Office Action, U.S. Appl. No. 14/084,255, dated Feb. 25, 2016.
Non-Final Office Action, U.S. Appl. No. 14/272,147, dated Jun. 17, 2016.
Non-Final Office Action, U.S. Appl. No. 14/869,762, dated Mar. 31, 2016.
Non-Final Office Action, U.S. Appl. No. 14/946,106, dated Jun. 23, 2016.
Non-Final Office Action, U.S. Appl. No. 15/168,359, dated Aug. 17, 2016.
Non-Final Office Action, U.S. Appl. No. 15/168,405, dated Aug. 3, 2016.
Notice of Allowance, U.S. Appl. No. 12/391,008, dated Dec. 22, 2015.
Notice of Allowance, U.S. Appl. No. 13/749,095, dated Apr. 7, 2016.
Notice of Allowance, U.S. Appl. No. 14/476,500, dated May 19, 2016.

(56) References Cited

OTHER PUBLICATIONS

Notice of Allowance, U.S. Appl. No. 15/167,614, dated Aug. 26, 2016.
Response to Final Office Action, U.S. Appl. No. 11/946,002, dated Mar. 29, 2016.
Response to Final Office Action, U.S. Appl. No. 13/749,095, dated Feb. 17, 2016.
Response to Non-Final Office Action, U.S. Appl. No. 13/923,093, dated May 2, 2016.
Response to Non-Final Office Action, U.S. Appl. No. 14/011,998, dated May 6, 2016.
Response to Non-Final Office Action, U.S. Appl. No. 14/084,255, dated May 23, 2016.
Response to Non-Final Office Action, U.S. Appl. No. 14/869,762, dated Jun. 29, 2016.
Response to Restriction, U.S. Appl. No. 14/335,431, dated Aug. 31, 2016.
Restriction Requirement, U.S. Appl. No. 14/335,431, dated Aug. 12, 2016.

\* cited by examiner

EMPLOYING THE CUSTOMIZED SHAPE MATCH HIP GUIDE

PREPARE THE HIP REGION OF THE PATIENT FOR AN ARTHROPLASTY PROCEDURE, WHICH INCLUDES ACCESSING THE PATIENT'S ACETABULUM.
[BLOCK 205]

↓

CUSTOMIZED SHAPE MATCH HIP GUIDE THAT INCLUDES A DIRECTIONAL ROD AND A SEMI HEMISPHERICAL HEAD WITH A SURFACE THAT IS A NEGATIVE OF THE SURFACE CONTOUR OF THE PATIENT'S ACETABULAR CUP IS MATINGLY RECEIVED IN THE PATIENT'S ACETABULAR CUP, WHEREIN THE MATING SURFACE OF THE HEAD OF THE GUIDE IS INTERDIGITATED WITH THE INNER SURFACE OF THE ACETABULAR CUP.
[BLOCK 210]

↓

SURGEON "EYEBALLS" THE ORIENTATION OF THE DIRECTIONAL ROD AND REMOVES THE GUIDE FROM THE PATIENT'S ACETABULAR CUP.
[BLOCK 215]

↓

SURGEON REAMS OR OTHERWISE PREPARES THE PATIENT'S ACETABULAR CUP FOR IMPLANTATION OF THE PROSTHETIC CUP.
[BLOCK 220]

↓

SURGEON REPLICATES THE SAME ORIENTATION OF THE DIRECTIONAL ROD WITH THE REAMER.
[BLOCK 225]

→ CONTINUED IN [BLOCK 230] IN FIG. 1G

FIG. 1F

```
                              ┌─────────────────────────────────────────────┐
                              │  PREPARE THE HIP REGION OF THE PATIENT FOR AN│
   EMPLOYING                  │  ARTHROPLASTY PROCEDURE, WHICH INCLUDES      │
      THE                     │  ACCESSING THE PATIENT'S ACETABULUM.         │
   CUSTOMIZED                 │              [BLOCK 240]                     │
   SHAPE MATCH                └─────────────────────────────────────────────┘
   HIP GUIDE WITH
   AN OUTRIGGER
      DEVICE
```

EMPLOYING THE CUSTOMIZED SHAPE MATCH HIP GUIDE WITH AN OUTRIGGER DEVICE

- PREPARE THE HIP REGION OF THE PATIENT FOR AN ARTHROPLASTY PROCEDURE, WHICH INCLUDES ACCESSING THE PATIENT'S ACETABULUM. [BLOCK 240]

- CUSTOMIZED SHAPE MATCH HIP GUIDE THAT INCLUDES A DIRECTIONAL ROD, A FIRST COUPLER DEVICE WHICH IS PART OF AN OUTRIGGER DEVICE AND ENGAGES WITH THE DIRECTIONAL ROD, AND A SEMI HEMISPHERICAL HEAD WITH A SURFACE THAT IS A NEGATIVE OF THE SURFACE CONTOUR OF THE PATIENT'S ACETABULAR CUP IS MATINGLY RECEIVED IN THE PATIENT'S ACETABULAR CUP, WHEREIN THE MATING SURFACE OF THE HEAD OF THE GUIDE IS INTERDIGITATED WITH THE INNER SURFACE OF THE ACETABULAR CUP. [BLOCK 245]

- A SECOND COUPLER DEVICE IS COUPLED TO THE FIRST COUPLER. [BLOCK 250]

- A REFERENCE ROD THAT EXTENDS THROUGH THE SECOND COUPLER DEVICE IS IMBEDDED IN THE PATIENT'S BONE OF THE HIP REGION, WHEREIN THE REFERENCE ROD IS GENERALLY PARALLEL TO THE GUIDE AND DIRECTIONAL ROD. [BLOCK 255]

- THE HIP GUIDE IS REMOVED FROM THE ACETABULAR CUP AND THE OUTRIGGER DEVICE WHILE MAINTAINING THE OUTRIGGER DEVICE IN THE SAME ORIENTATION. [BLOCK 260]

- CONTINUED IN [BLOCK 265] IN FIG. 1I

FIG. 1H

MRI Scanning Parameters For Model Generation

| Parameter | Value | |
|---|---|---|
| Field Of View | 200mm x 200mm | Include key anatomical landmarks around the cup model |
| Scan Direction | Coronal | Orthogonal scan angle for accurate modeling the fovea |
| Slice Thickness | 2mm | Minimum value for MRI signal noise reduction |
| Matrix | 512 x 512 | High resolution for the segmentation, pixel=0.39mm |

FIG. 2B

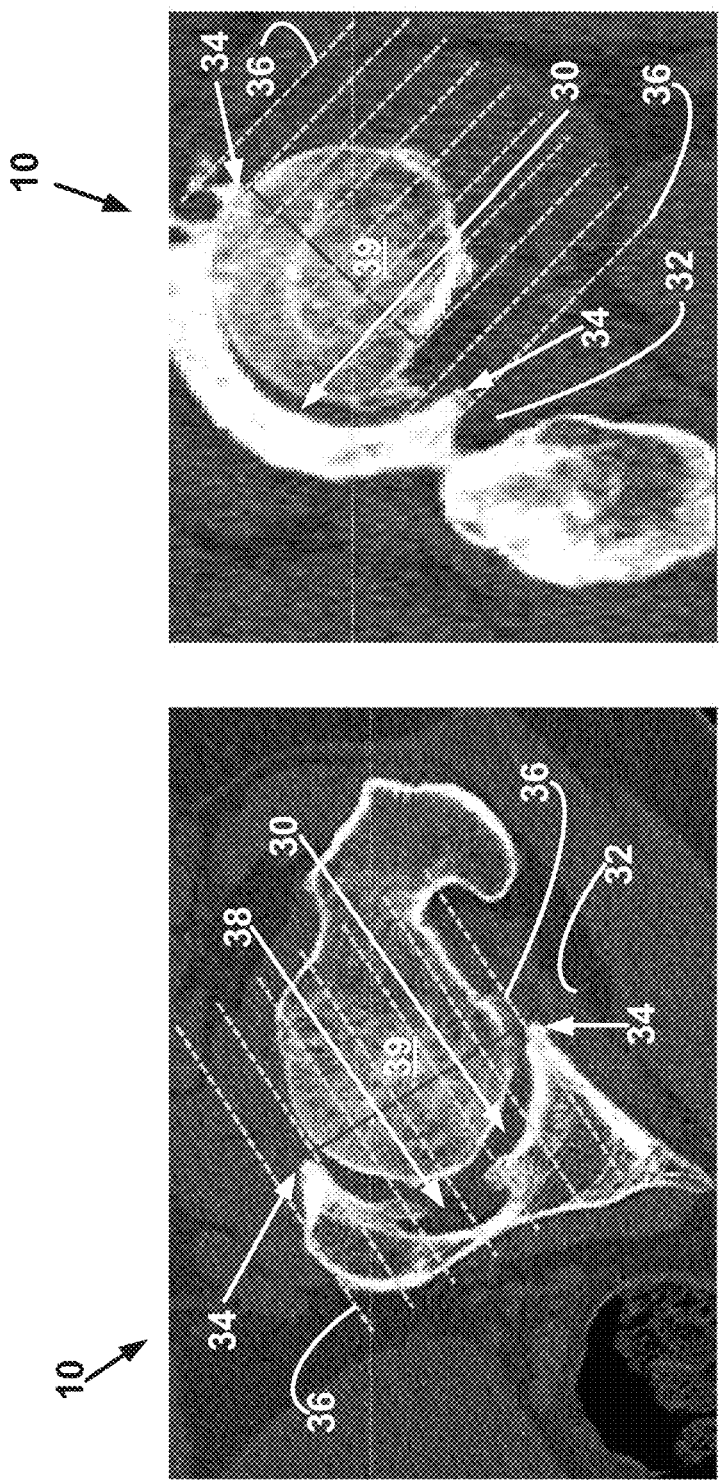

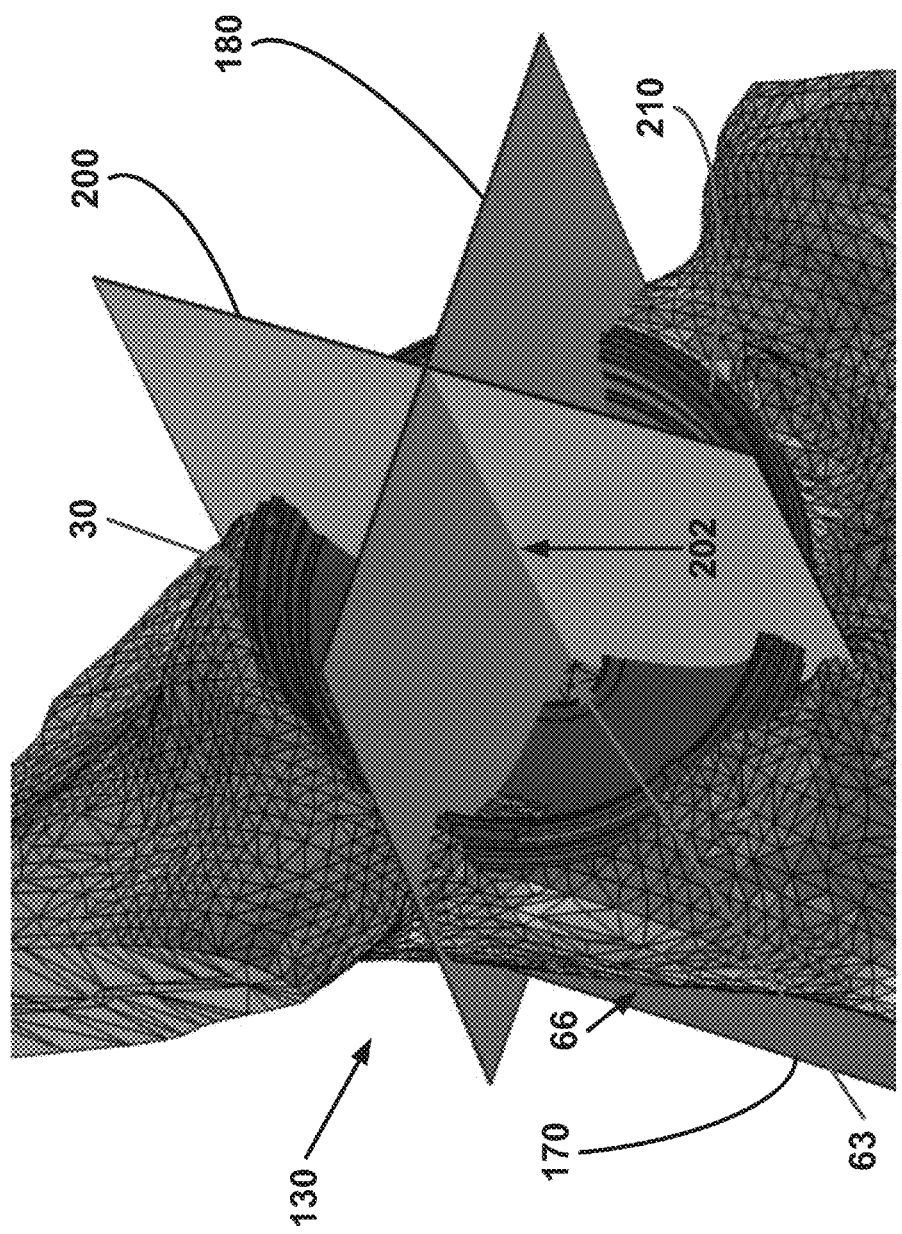

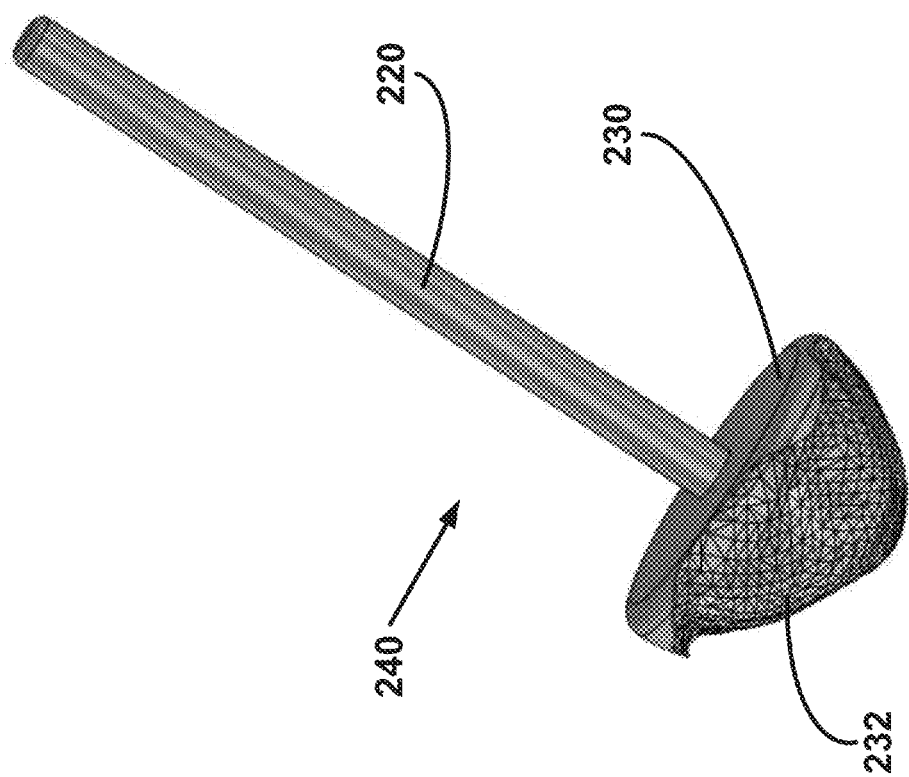

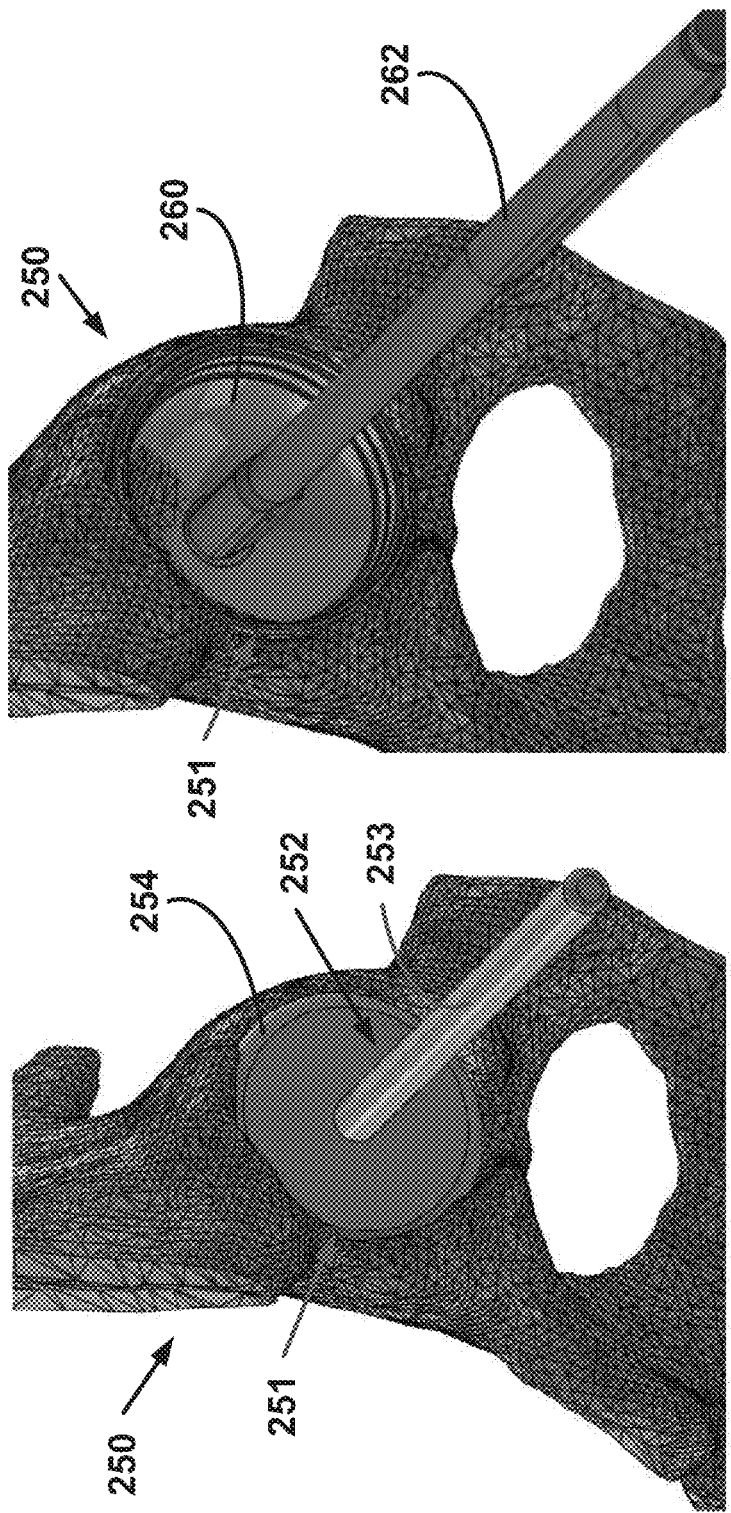

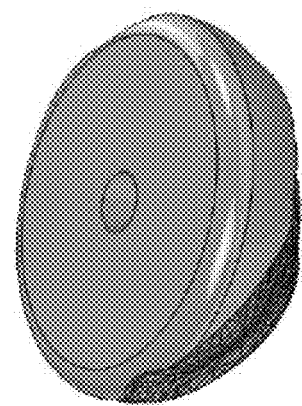
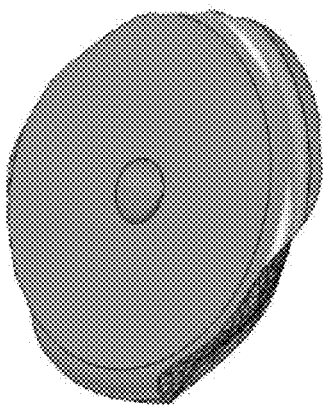
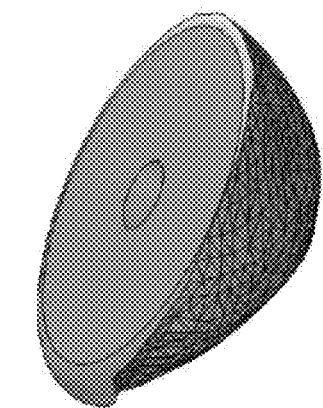
FIG. 19

CUSTOMIZED ACETABULAR CUP POSITIONING GUIDE AND METHOD OF GENERATING AND EMPLOYING SUCH A GUIDE

CROSS REFERENCE TO RELATED APPLICATIONS

The present application is a divisional application of U.S. application Ser. No. 13/960,498 filed Aug. 6, 2013, which application claims priority under 35 U.S.C. § 119 to U.S. provisional patent application 61/794,662, which was filed Mar. 15, 2013, entitled "ACETABULAR CUP POSITIONING." Both applications are hereby incorporated by reference in their entireties into the present application.

FIELD OF THE INVENTION

Aspects of the presently disclosed technology relate to medical apparatuses, systems, and methods. More specifically, the presently disclosed technology relates to a customized acetabular cup positioning guide and surgical systems and methods for generating and employing the guide and implanting an acetabular cup with the guide.

BACKGROUND OF THE INVENTION

Over time and through repeated use, bones and joints can become damaged or worn. For example, repetitive strain on bones and joints (e.g., through athletic activity), traumatic events, and certain diseases (e.g., osteoarthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned or an implant can be implanted into the damaged region. Arthroplasty procedures may take place in any of a number of different regions of the body, such as a knee, a hip, a shoulder, or an elbow.

One type of arthroplasty procedure is a total hip arthroplasty ("THA") procedure, which consists of replacing both the acetabulum, also known as acetabular cup, and the femoral head with prosthetic implants. Another type of arthroplasty procedure is a hemi or half hip replacement, which consists of replacing just the femoral head with a prosthetic implant. The hip joint may have been damaged by, for example, arthritis (e.g., severe osteoarthritis or degenerative arthritis), trauma, or a rare destructive joint disease. Typically, a THA procedure is conducted to relieve pain due to osteoarthritis or to remedy severe joint damage as part of hip fracture treatment.

The hip is one of the largest joints in the human body. The hip consists of a ball and socket, wherein the socket is formed by the acetabulum, which is part of the pelvis bone. The ball, in the ball and socket system, is the femoral head, which is at the proximal end of the femur. The surfaces of the ball and socket are covered with articular cartilage, a smooth tissue that cushions the ends of the bones and enables femoral head and the acetabulum to move easily. A thin tissue called synovial membrane surrounds the hip joint. In an otherwise healthy hip joint, this membrane makes a small amount of fluid that lubricates the cartilage and eliminates almost all friction during hip movement. Bands of ligaments connect the ball to the socket and provide stability to the joint.

During a THA procedure, a damaged portion of bone in the femoral head may be removed and replaced with a femoral prosthesis or implant, and a damaged portion of the bone and cartilage in the acetabulum may be removed by reaming, scraping, cleaning or otherwise preparing of the acetabular surface to receive an implanted prosthesis, such as a prosthetic acetabular cup. After the damaged portion of the femoral head is removed, the femoral prosthesis, which includes a stem, may be cemented or simply press fitted into the patient's femur. Similarly, the acetabular cup may be screwed, pinned, cemented, or otherwise coupled to the patient's acetabulum. The acetabular cup can additionally include an osseointegrated surface to enhance the fusion of the bone to the implant. The interface between the acetabular cup and the femoral prosthesis is the ball and socket joint, or the articular interface. The specifications for the articular interface (e.g., make, model, size, material) vary depending on the patient's bony anatomy, health, activity level, and associated risks involved with the procedure.

Implants that are implanted into a damaged region may provide support and structure to the damaged region and may help to restore the damaged region, thereby enhancing its functionality. Prior to implantation of an implant in a damaged region, the damaged region is prepared to receive the implant. For example, in a hip arthroplasty procedure, one or more of the bones in the hip area, such as the femur and/or the acetabulum, may be treated (e.g., cut, drilled, reamed, and/or resurfaced) to provide one or more surfaces that can align with the implant and thereby accommodate the implant.

Accuracy in implant alignment is an important factor to the success of a THA procedure. Preparing a patient's acetabulum for implanting of a prosthetic acetabular cup can be challenging because of the unique contouring shape of the patient's acetabulum, and because the pelvic bone does not easily lend itself to resections, as in an arthroplasty procedure involving implants to the femur or tibia. These factors underscore the importance of properly preparing the acetabulum prior to a THA procedure and properly aligning the acetabular cup to the acetabulum. A one to two millimeter translational misalignment may result in imbalanced ligaments and thus may significantly affect the outcome of the procedure. For example, implant misalignment may result in intolerable post-surgery pain and also may prevent the patient from having stable leg flexion. In particular, the patient's joint may not be restored to its natural alignment with respect to the knee and ankle centers, which can result in pain and difficulty in adjustment to the new alignment.

To achieve accurate implant alignment, prior to treating (e.g., cut, drilled, reamed, and/or resurfaced) any regions of a bone, it is important to correctly determine the location at which the treatment will take place and how the treatment will be oriented. In some methods, an arthroplasty guide may be used to position and orient a resection, sawing, or implantation instrument, such as a cutting, drilling, reaming, resurfacing, or impacting instrument on the regions of the bone. The arthroplasty guide may, for example, include referencing rods and one or more apertures and/or slots that are configured to accept such an instrument. However, under some methods, it is difficult to determine the proper orientation of an arthroplasty guide and ultimately of the positioning and alignment of an acetabular cup implant. Some methods utilize arthroplasty guides to provide orientation of the treatment relative to the regions of the bone. However, such guides often rely on a human to subjectively determine or "eyeball" rotational angles and the extent of the treatment. For example, when performing an acetabular cup implantation into the hip region of a patient, many guides rely on a surgeon to determine the proper orientation of the guide as well as how much of the bone to remove when mating the implanted prosthesis to the bone. More particularly, once a surgeon has begun reaming a patient's acetabulum or impacting/implanting the acetabular cup, it can be difficult and damaging to accurately stop the reaming or impacting/implanting and start anew.

Accordingly, there is a need in the art for a customized arthroplasty acetabular cup positioning guide, and surgical systems and methods for generating and employing the acetabular cup positioning guide that increases the accuracy of arthroplasty procedures.

SUMMARY OF THE INVENTION

Implementations described and claimed herein address the foregoing problems by providing a customized acetabular cup positioning guide as well as systems and methods for generating and employing the acetabular cup positioning guide for use in a hip replacement arthroplasty procedure.

A custom acetabular positioning guide and method of manufacturing and employing the guide are disclosed herein. In one implementation, the acetabular cup positioning guide includes: a directional rod extending from a semi-hemispherical blank or mold, which has a hemispherical surface that is a negative of the surface contour of the inside surface of the patient's acetabulum. The manufactured shape-match hemispherical surface of the hip guide matingly interdigitates with the corresponding inner surface of the patient's acetabulum and causes the directional rod to extend along a directional line that mimics a preoperatively planned axis. The axis defined by the directional rod is then used as a guide for implanting the prosthetic cup with an impactor shaft. While using the impactor shaft to drive the prosthetic cup into the acetabular cup of the patient, the surgeon tries to replicate the same orientation of the directional rod with the impactor rod.

In another implementation, the acetabular cup positioning guide includes a shape-match hip guide, which includes the directional rod and semi-hemispherical blank with a hemispherical surface that is a negative contour of the inside surface of the patient's acetabular cup, as described in the previous implementation. In addition, the positioning guide includes a first coupler half of an outrigger device that extends over the directional rod. A second coupler half of the outrigger device is coupled to the first coupler half as well as a reference rod that extends through the second coupler half to be imbedded in the bone of the hip region. The reference rod is held parallel to the directional rod by the outrigger device. The cup guide and directional rod are removed from the outrigger device, which stays implanted into the hip region of the patient in the original orientation. Subsequent to reaming the acetabular cup, wherein the reaming angle of the reamer may be guided by the coupler, which attaches the first coupler to the directional rod or like device, the prosthetic acetabular cup is then placed in the patient's acetabular cup. The outrigger device provides one angle (i.e., inclination angle), whereby the surgeon "eyeballs" the other angle (i.e., aversion angle).

In another implementation, the acetabular cup positioning guide includes a shape-match hip guide, which includes the directional rod and semi-hemispherical blank with a hemispherical surface that is a negative contour of the inside surface of the patient's acetabular cup, as described in the previous implementation. In addition, the positioning guide includes a silo device, which includes a barrel with a guide hole that slideably receives the directional rod. The silo device also includes a plurality of silo legs that extend from the barrel and are adapted for anchoring to the bone of the patient's hip region. The silo legs can be anchored to the hip region by pins, screws, or other devices. Once anchored to the hip region, the shape-match hip guide can be removed from the patient's acetabulum and thus the silo device. The patient's acetabulum is reamed in preparation for implantation of the prosthetic acetabular cup. The prosthetic acetabular cup is then inserted into the patient's acetabulum or acetabular cup and an impactor is inserted into the guide hole of the silo barrel via an access slot and is held in place against the prosthetic cup by reinstallation of a keyed side portion into the slot. As a result, the impactor is held against the prosthetic cup in proper alignment as established by the rod of the shape-match hip guide. The impactor, which is slidingly retained in the guide hole, may then be impacted against the prosthetic cup to seat the cup in the patient's acetabular cup. The silo and impactor can then be removed, leaving behind the implanted prosthetic acetabular cup.

Other implementations described and claimed herein provide a method of manufacturing the custom acetabular cup positioning guide. In one embodiment, the method of manufacturing the custom guide includes generating a plurality of MRI slices, CT slices, or other suitable medical images of a portion of a patient's bone to undergo an arthroplasty procedure. These images are used in the pre-operative planning phase of the procedure and can include medical imaging in axial, coronal, and sagittal planes.

In one embodiment of the method of manufacturing the custom acetabular cup positioning guide, the operation includes placing anatomical landmarks around the bone boundaries in the medical image slices. For example, placing the landmark points may include a user at a user interface employing at least one of a mouse, keyboard, pen-and-tablet system, touch screen system, or spatial input device to place landmark points. The bone boundaries may include lines representative in the medical imaging slices of acetabular cup boundaries, among others.

In one embodiment of the method of manufacturing the custom acetabular cup positioning guide, the operation includes defining a triangle in a coronal image slice of the hip region of the patient that extends between certain landmarks. The triangle can be defined across the patient's anterior pelvic area, wherein the triangle's three corners are respectively located at the right anterior-superior ilium symphysis ("ASIS-R"), the left anterior-superior ilium symphysis ("ASIS-L"), and the pubic symphysis. A pelvic axis line is defined to extend across the right teardrop and the left teardrop of the pelvis. Both legs of the triangle can be seen to extend immediately adjacent a proximal point of the acetabular cup. The triangle can additionally include a frontal axis that divides the triangle at its height by extending between a midpoint of the base line of the triangle that extends between the ASIS-R and the ASIS-L. The frontal axis is used to check for pelvic tilt. A "check" can be made that the frontal axis is perpendicular to the pelvic axis. Additional measurements can be taken with respect to the triangle; the measurements can include determining the angle between the pelvic axis and the target side line, wherein the target side line is the leg of the triangle that extends between the pubic symphysis and the anterior-superior ilium symphysis on the surgical target side (i.e., ASIS-R or ASIS-L). A 45 degree angle or any value that is required as a surgical goal prescribed by the surgeon can also be defined between an axis line and the pelvic axis, wherein the intersection of the axis line and the pelvic axis is about the teardrop of the pelvis on the surgical target side. The 45 degree angle that was just described can be moved to intersect the target side line in such a manner that the axis line projects generally along the axis of the femoral head and the femoral neck of the surgical target side. The axis line now generally defines a hip guide pin axis, which defines the inclination of the prosthetic acetabular cup.

In one embodiment of the method of manufacturing the custom acetabular cup positioning guide, the operation includes converting the MRI slices, CT slices, or similar medical images into at least one three dimensional model that represents the portion of the patient's body to undergo an arthroplasty procedure. The three dimensional model can include a portion of the pelvis and the contour surface of the acetabular cup, the contour surface being a generally identical replication of the inner surface of the patient's acetabular cup or acetabulum. The pre-operative planning process explained with respect to the two dimensional medical slices is replicated with respect to the three dimensional model. A plane connects the proximal point of the public symphysis with a proximal point of the acetabular cup. A second plane is provided such that it intersects the first plane at the proximal point of the acetabular cup. The second plane, also referred to as an inclination plane, extends through the center point of the acetabular cup. A third plane, referred to as an anteversion plane, is positioned to evenly divide the anterior and posterior walls of the acetabular cup and also pass through the center of the acetabular cup. The anteversion plane is perpendicular to the inclination plane and it divides the acetabular cup in half. The intersection of the two planes defines an axis line that approximates a center axis of the acetabular cup.

In one embodiment of the method of manufacturing the custom acetabular cup positioning guide, the operation includes a three dimensional model of a candidate prosthetic acetabular cup occupying the acetabular cup of the three dimensional surface model. The prosthetic cup is positioned relative to the inclination and anteversion planes such that a center axis of the cup is coaxial with the axis defined by the intersection of the planes. A three dimensional model of a directional rod can be included, wherein the directional rod is positioned so as to be coaxial with the axis defined by the intersection of the planes.

In one embodiment of the method of manufacturing the custom acetabular cup positioning guide, the operation includes replacing the three dimensional model candidate prosthetic cup with a three dimensional model of a semi-hemispherical blank or mold, while maintaining the directional rod in its orientation relative to the intersection of the inclination and anteversion planes. The hemispherical surface of the semi-hemispherical blank or mold extends along the surface contour of the inside surface of the acetabular cup of the three dimensional surface model. As a result, the blank or mold is caused to assume a surface contour that is a negative of the surface contour of the inside surface of the acetabular cup of the three dimensional surface model.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 1F-1G are flow chart diagrams outlining the surgical method of employing the acetabular cup positioning guide.

FIGS. 1H-1I are flow chart diagrams outlining the surgical method of employing the acetabular cup positioning guide with an outrigger device.

FIG. 2B is a table of MRI scanning parameters used in the generation of the medical image slices depicted in FIG. 2A.

FIGS. 3A and 3B are, respectively, axial and sagittal plane medical image slices of the patient's acetabular cup.

FIGS. 13A-13B are three dimensional surface models of a patient's acetabular cup wherein a candidate prosthetic acetabular cup without and with a directional rod extending along the hip guide pin axis occupies the acetabular cup of the three dimensional surface model.

FIG. 15 is a 3D model of a shape-match hip guide that includes a directional rod extending from a semi-hemispherical blank or mold, which has the hemispherical surface that is a negative of the surface contour of the inside surface of the acetabular cup of the 3D surface model.

FIGS. 16A-16B are views of a patient's actual hip region including the acetabular cup in the process of receiving an actual prosthetic acetabular cup via a shape-match hip guide.

FIG. 19 illustrates three different embodiments of the custom fit mating head of the hip guide described herein.

DETAILED DESCRIPTION

Aspects of the presently disclosed technology involve customized acetabular cup guides 252, systems 3, and methods of using the same during arthroplasty procedures. In one aspect, the guides 252 are customized to fit specific bone surfaces of a hip joint 12 of a specific patient 11 to treat (e.g., cut, drilled, reamed, and/or resurfaced) the bone to provide one or more surfaces that can align with an implant and thereby accommodate the implant.

Figure 1A:
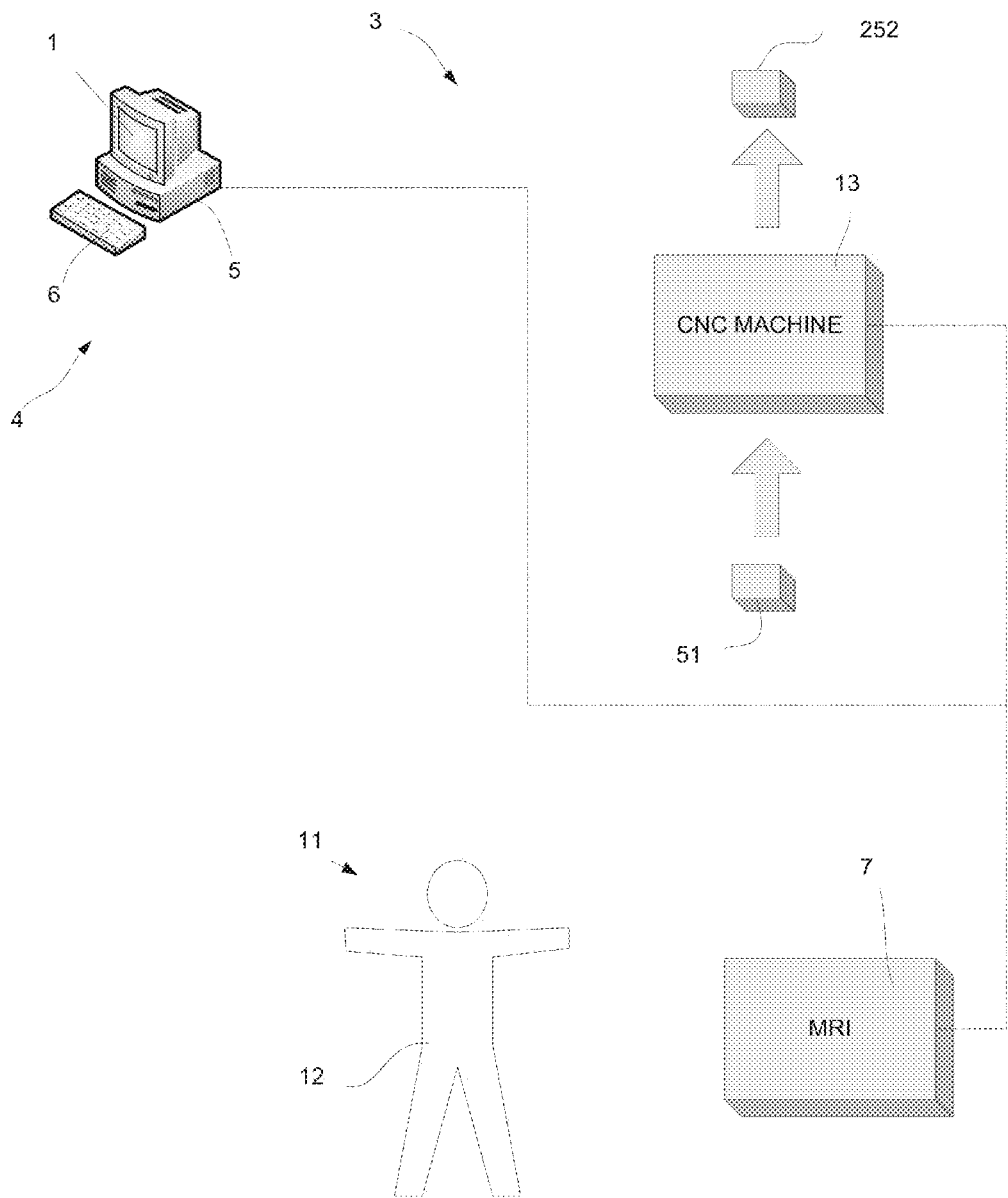
FIG. 1A is a schematic diagram of a system for employing the customized acetabular cup guide production method disclosed herein.

For an overview discussion of the systems 3 for, and methods of producing the customized acetabular cup positioning guides 252, reference is made to FIG. 1A. FIG. 1A is a schematic diagram of a system 3 for employing the customized acetabular cup guides production method disclosed herein. FIGS. 1B-1E are flow chart diagrams outlining the acetabular cup positioning guide production method disclosed herein. The following overview discussion can be broken down into four sections.

Figure 1B:
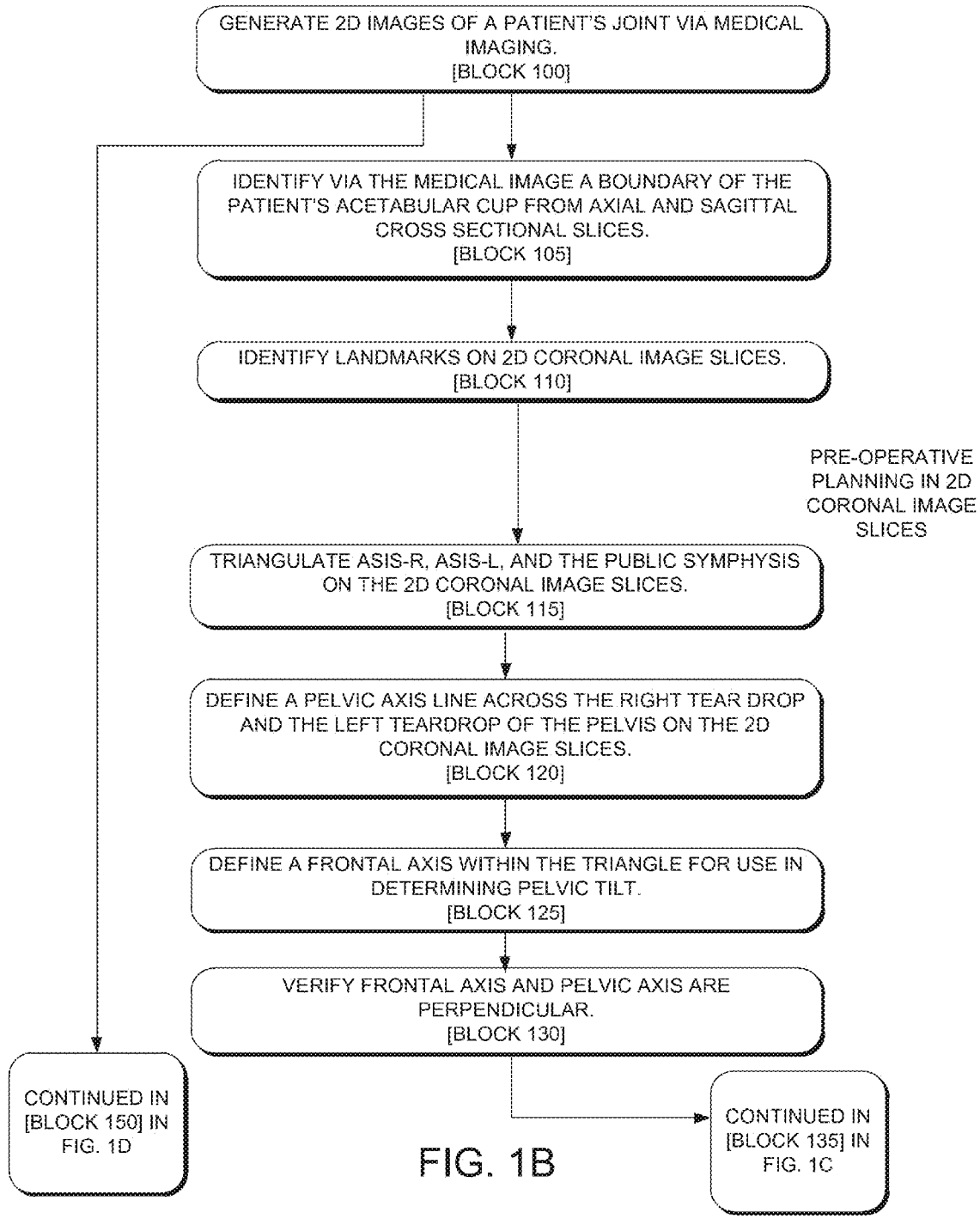
FIGS. 1B-1E are flow chart diagrams outlining the acetabular cup positioning guide production method disclosed herein.
Figure 1C:
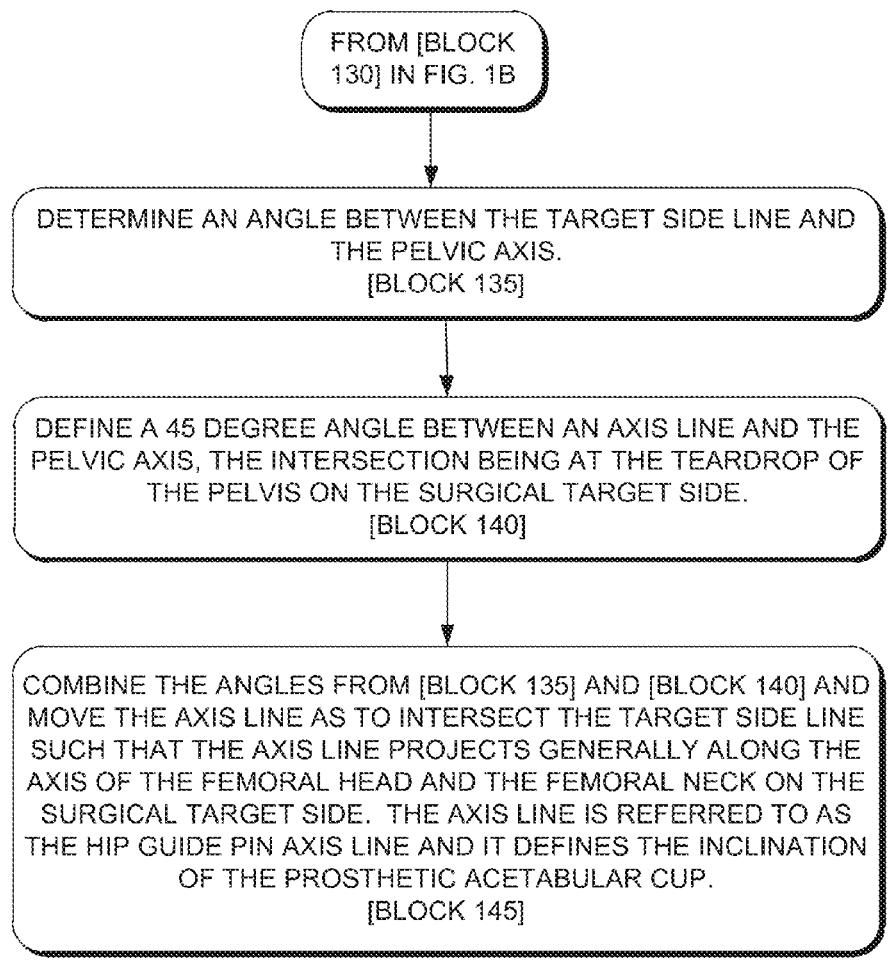

The first section, which is discussed with respect to FIGS. 1A-1C, pertains to an example method of determining, from two dimensional (2D) medical images, a hip guide pin axis line for use in the preoperative planning stages of an arthroplasty procedure. The hip guide pin axis line generally extends along the patient specific axis of the femoral head and femoral neck, wherein a prosthesis that is implanted with respect to the hip guide pin axis line will restore the patient's joint to its pre-degenerative orientation. In other words, in some embodiments, the patient's joint may be restored to its natural alignment, whether valgus, varus or neutral.

The system 3 for producing the customized guide 252 may be such that the system 3 initially generates the preoperative planning ("POP") associated with the jig in the context of the POP resulting in the patient's hip being restored to its natural alignment. The disclosure, however, should not be limited to methods resulting in natural alignment only, but should, where appropriate, be considered as applicable to methods resulting in alignments other than a natural alignment.

Figure 1D:
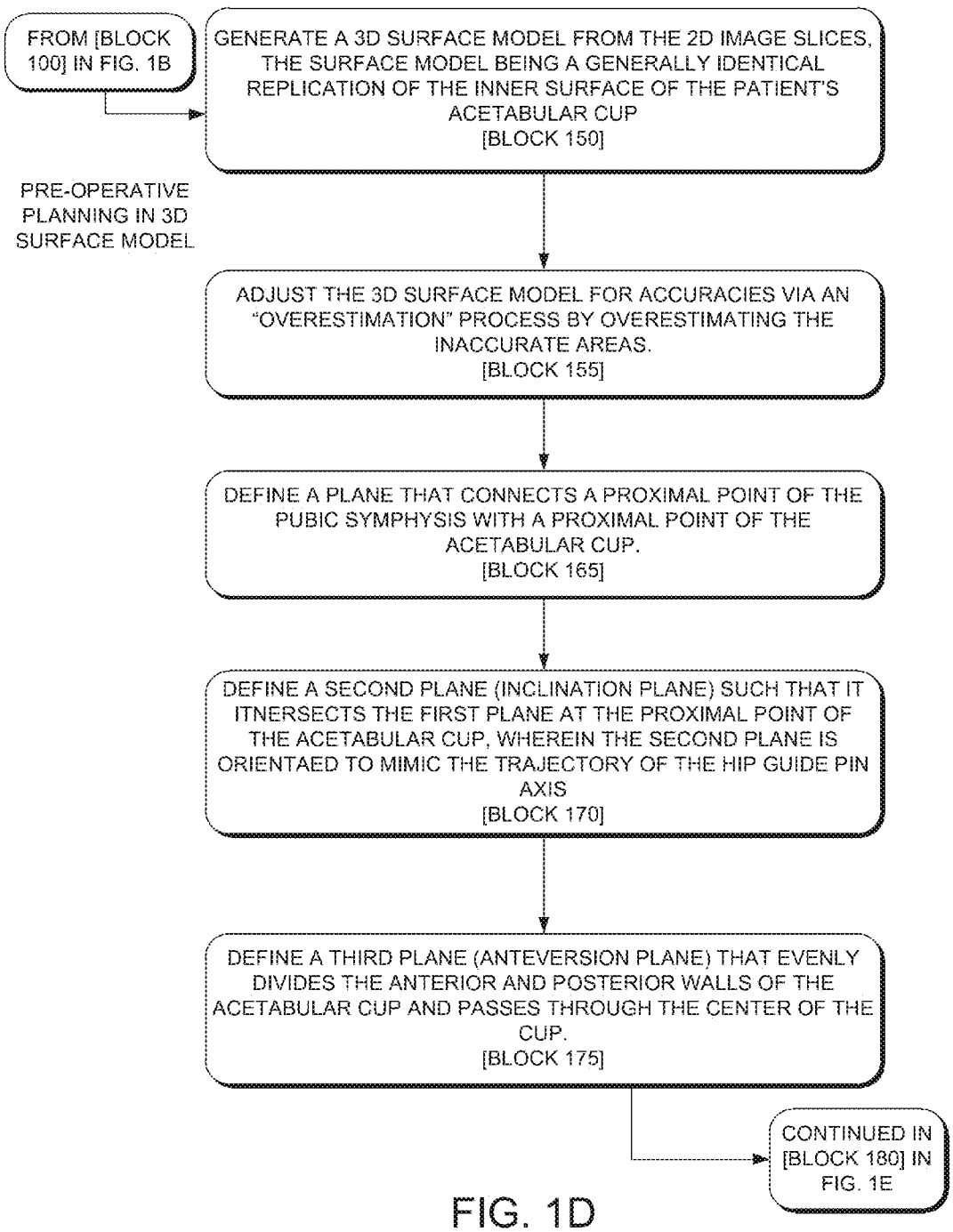
Figure 1E:
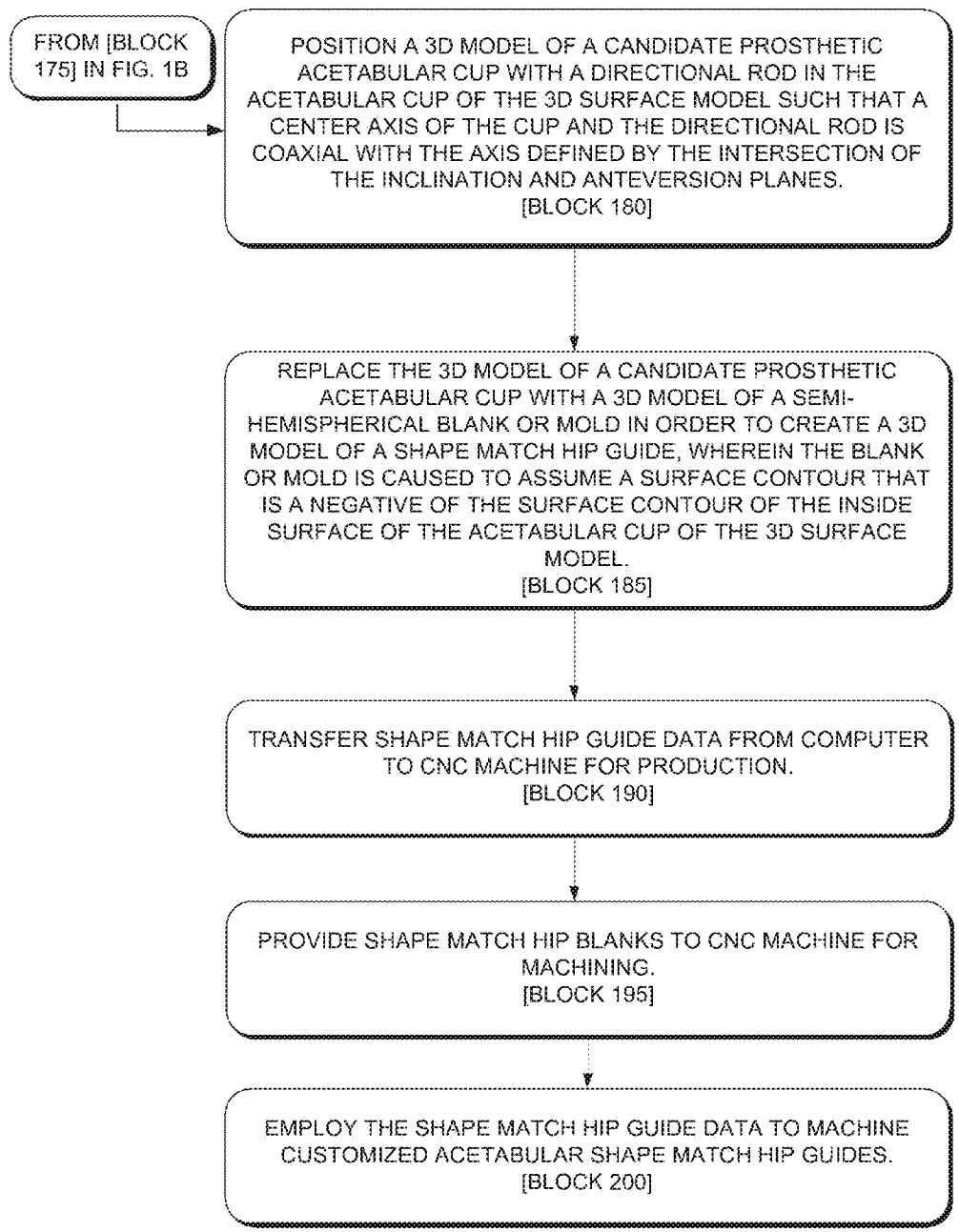
Figure 1G:
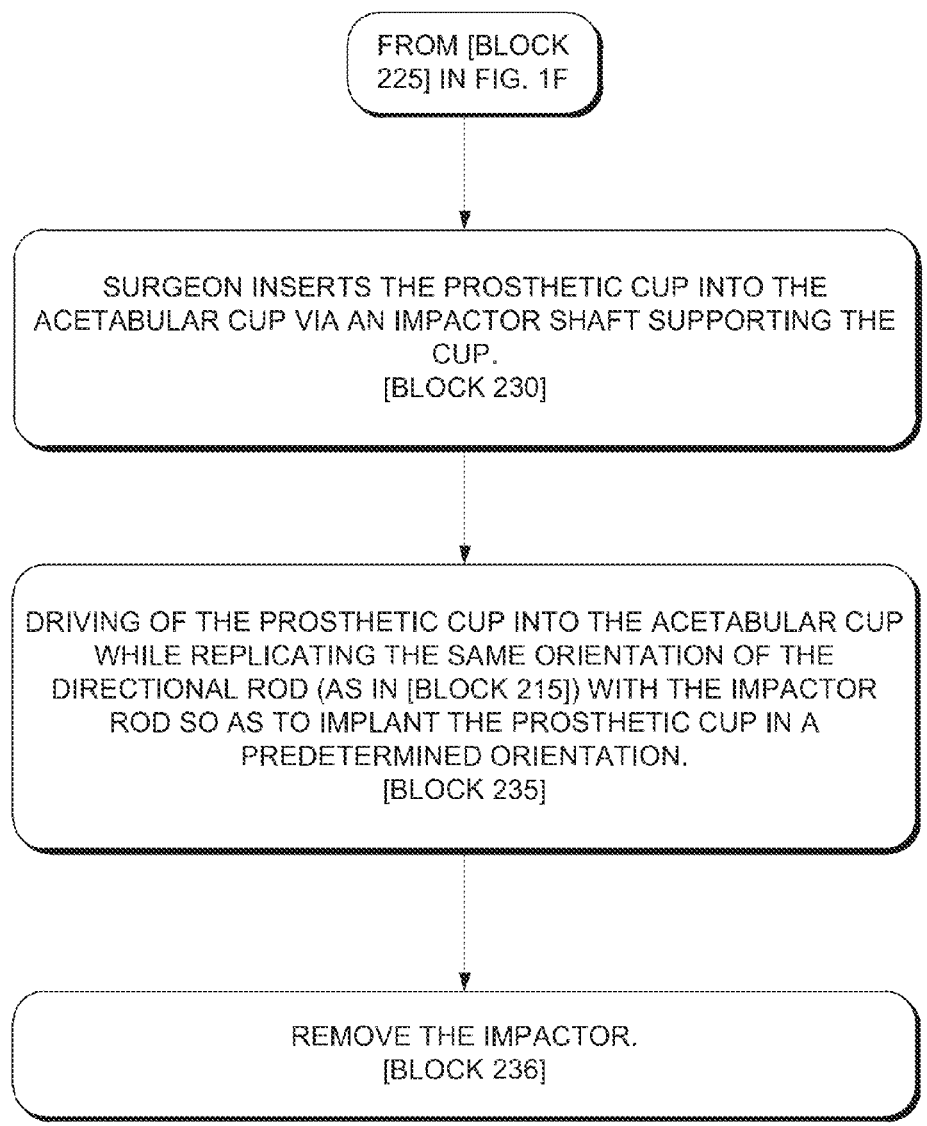
Figure 1I:
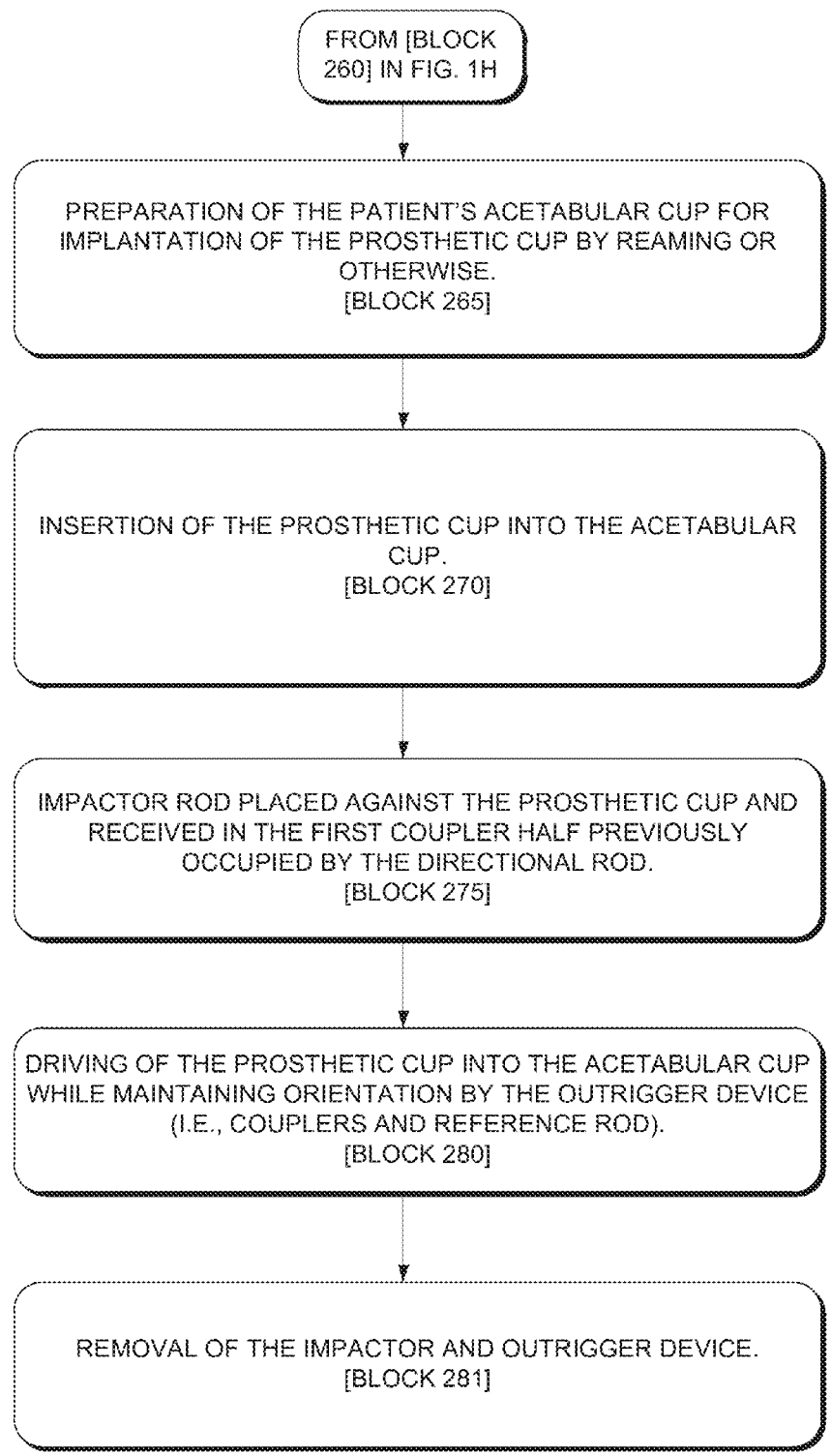
Figure 1J:
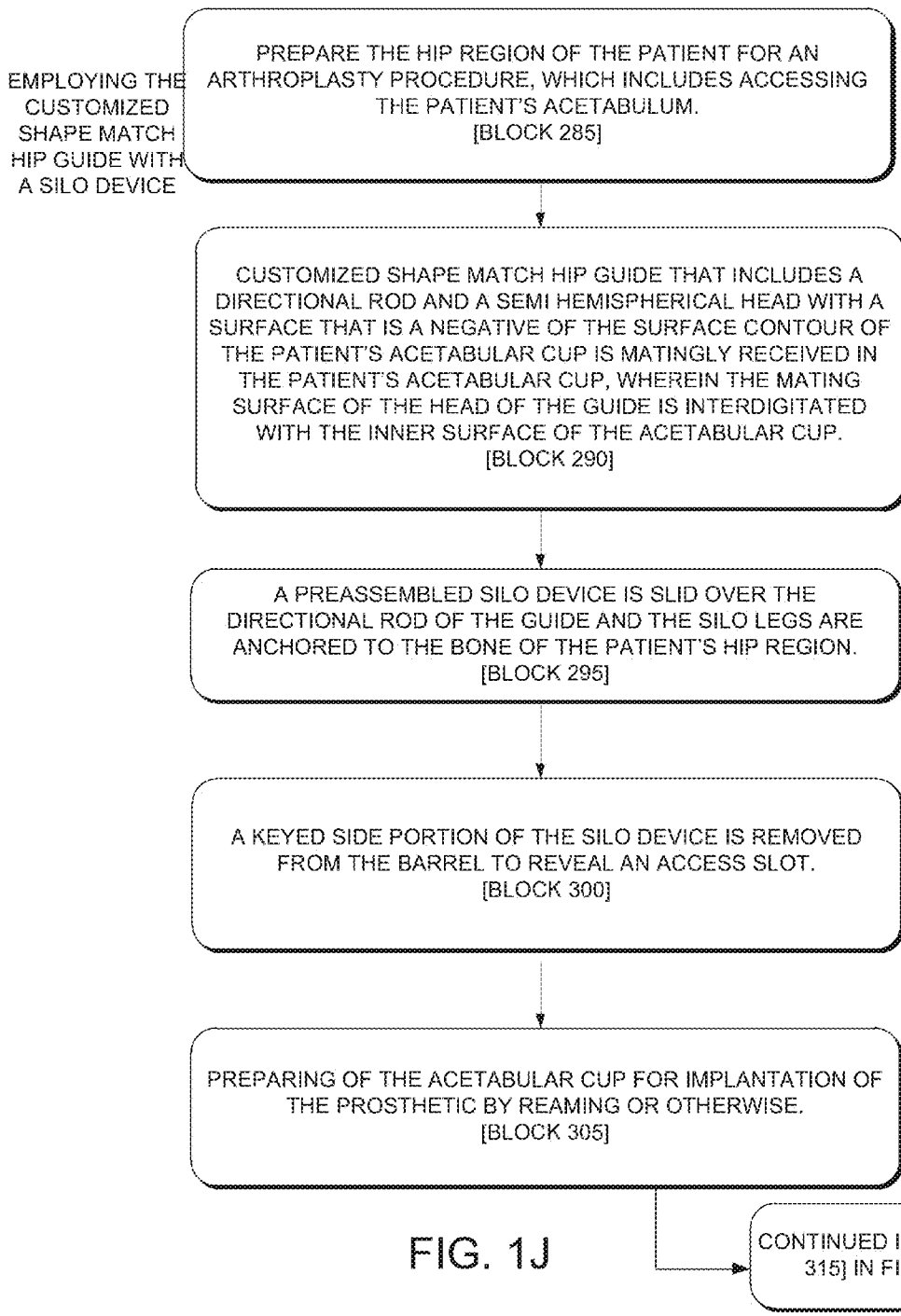
FIGS. 1J-1K are flow chart diagrams outlining the surgical method of employing the acetabular cup positioning guide with a silo device.
Figure 1K:
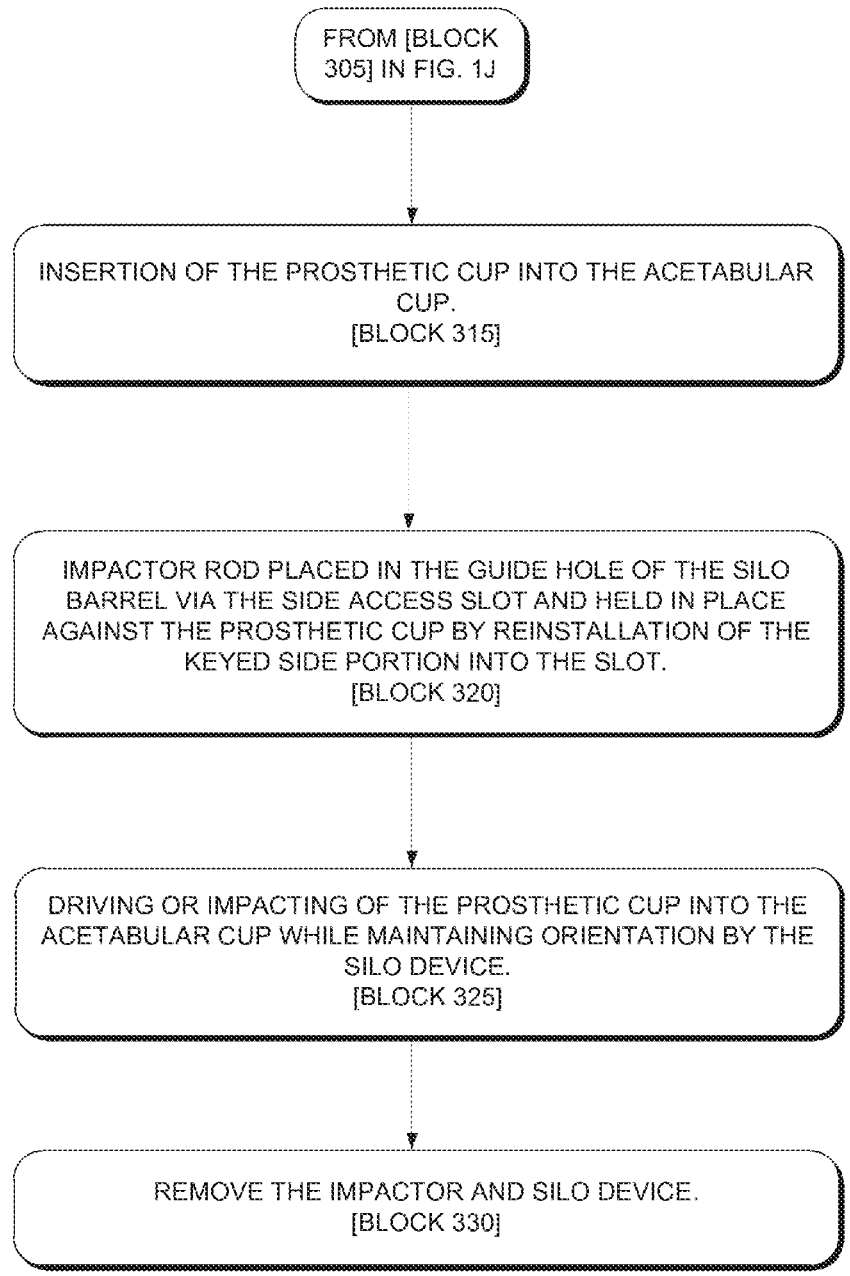

The second section, which is discussed with respect to FIGS. 1A and 1D-1E, pertains to an example method of generating a three dimensional (3D) bone model of a portion of a patient's body to undergo a hip replacement procedure, in particular a patient's acetabular cup, and generating a 3D shape-match hip guide model with a head that is a negative of the surface contour of a patient's acetabular cup and a directional rod that aligns with the hip guide pin axis line when the head matingly interdigitates with the patient's acetabular cup. The 3D shape-match hip guide model can then be machined in a CNC machine 13 or other suitable rapid prototype machine to produce a custom guide 252, which is sent to the surgeon, and employed in an arthroplasty surgical procedure.

The third section, which is discussed with respect to FIGS. 1A and 1F-1K, pertains to a method of employing the shape-match guide in a surgical procedure. In certain embodiments, the shape-match hip guide is employed by itself and in certain embodiments the shape-match hip guide is employed in conjunction with an outrigger or silo alignment device.

Figure 20:
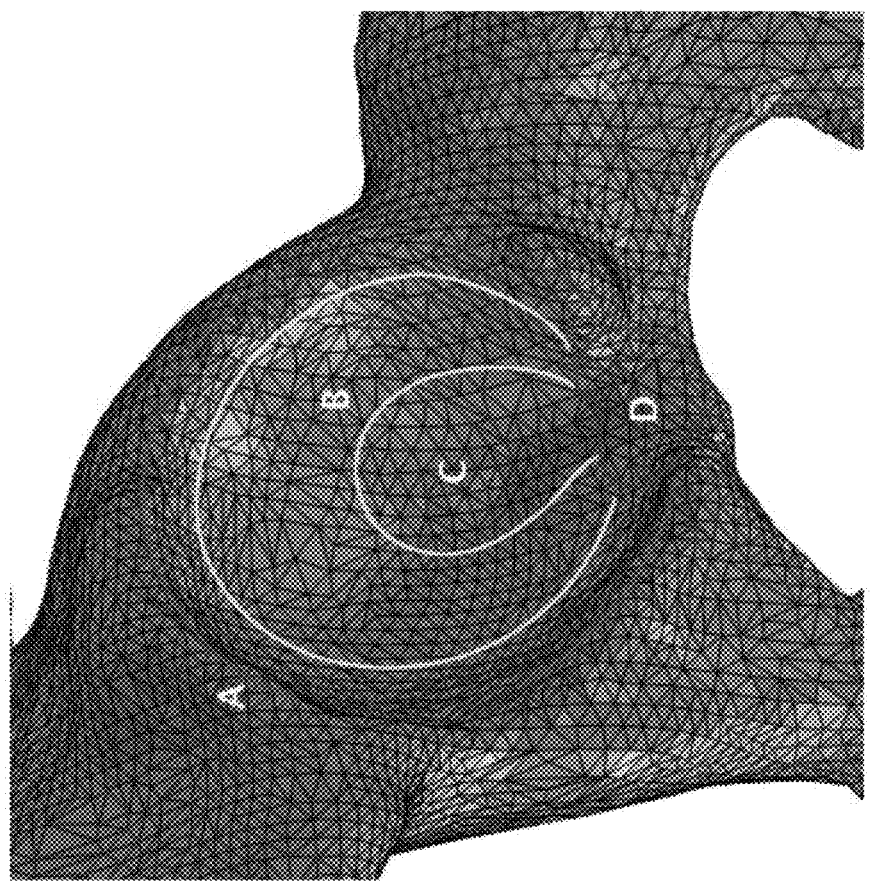
FIG. 20 depicts four different potential mating surface regions that may or may not be integrated into the mating surface of the head of the hip guide described herein.

The fourth section, which is discussed with respect to FIGS. 19-20, pertains to the mating head surface of the custom acetabular hip guide 252 as it relates to placement in a patient's acetabular cup.

I. POP with 2D Medical Images.

The system 3 in FIG. 1A includes a computer 4 having a CPU 5, a monitor or screen 1 and operator interface controls 6. The computer 4 is linked to a medical imaging system 7, such as a CT or MRI machine 7, and a computer controlled machining system 13, such as a CNC milling machine 13 or other rapid prototype machine (e.g., stereolithography apparatus ["SLA" Machine]). As indicated in FIG. 1A, a patient 11 has a hip joint 12 to be replaced. The patient 11 has the joint 12 scanned in the imaging machine 7. The imaging machine 7 makes a plurality of scans 10 of the joint 12, wherein each scan pertains to a thin slice of the joint 12.

Figure 2A:
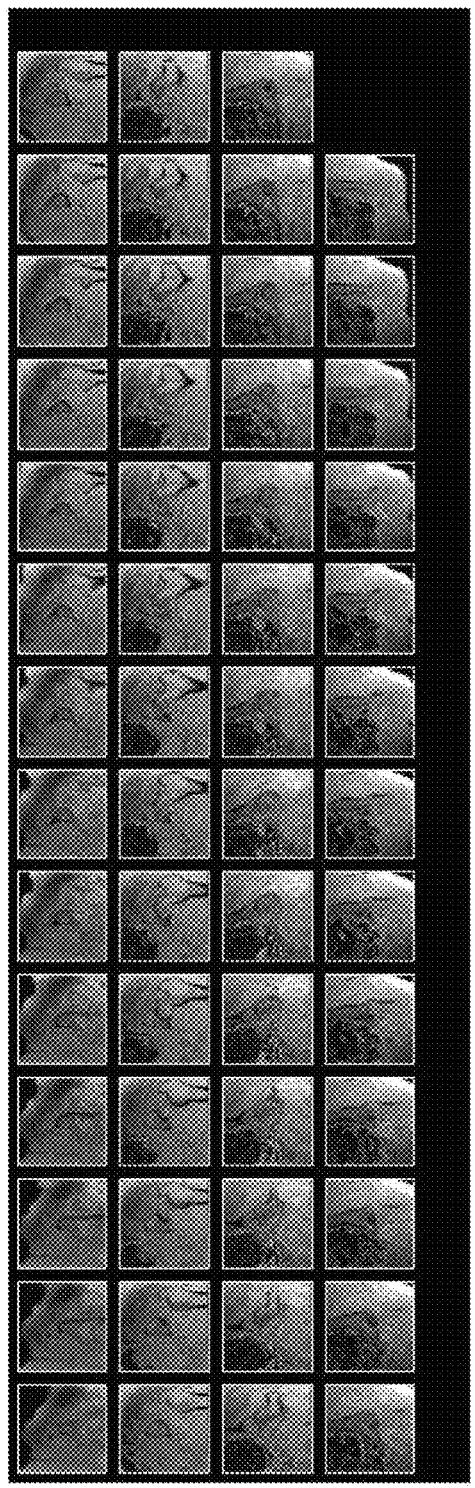
FIG. 2A illustrates a series of medical imaging scan slices generated via MRI, CT or other medical imaging techniques.

As can be understood from FIGS. 1B and 2A the plurality of scans 10 is used to generate a plurality of 2D images of the joint [BLOCK 100]. Where, for example, the joint is a hip 12, the 2D images will include the femur, acetabular cup, and pelvic area generally. The imaging may be performed via CT or MRI 7.

As can be understood from FIGS. 1A and 1D, the 2D images [BLOCK 100] are sent to the computer 4 for creating computer generated 3D models [BLOCK 150], which are used to generate a 3D shape-match hip guide model 240. FIG. 2A illustrates a series of medical imaging scan slices 10 generated via MRI, CT 7 or other medical imaging techniques. These image slices 10 are employed in the preoperative planning and shape-match hip guide designing methodology discussed in the following pages.

FIG. 2B is a table of MRI scanning parameters used in the generation of the image slices 10 depicted in FIG. 1A.

FIGS. 3A and 3B are, respectively, axial and sagittal MRI image slices 10 of the patient's acetabular cup 30 at the most axial and sagittal representative cross section of the cup 30. In other words, the images slices 10 of FIGS. 3A and 3B are at those axial and sagittal cross sections that show the cup 30 at its largest diameter and most rounded point as viewed axially and sagittally, respectively. The boundary of the cup 30 can be determined in the axial and sagittal cross-sectional slices illustrated in FIGS. 3A and 3B [BLOCK 105]. The bone boundaries are segmented to create bone contour lines.

Figure 7:
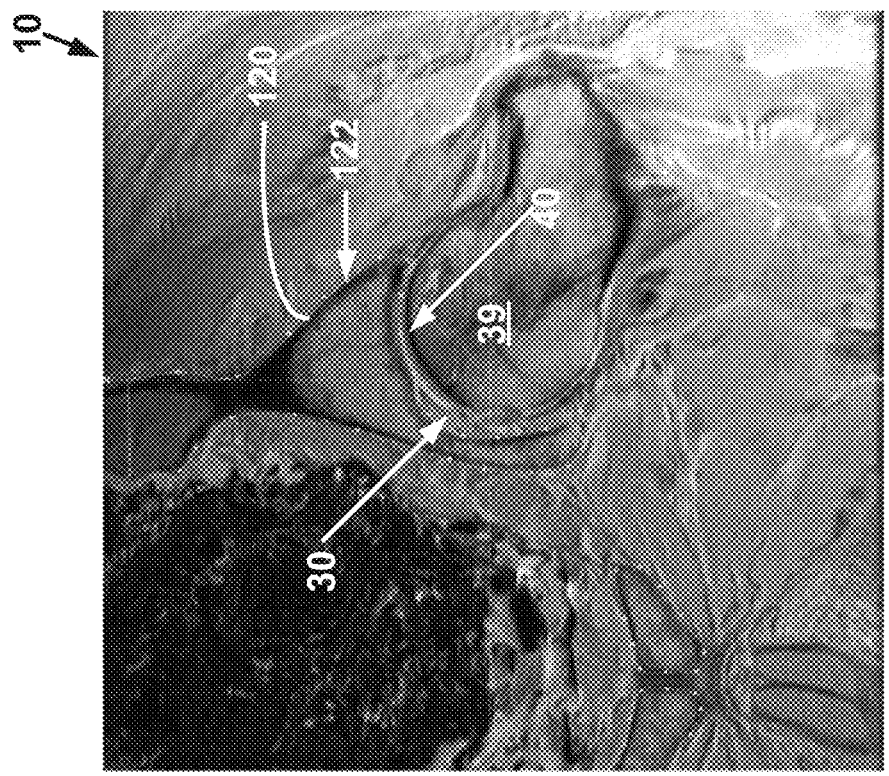
FIG. 7 is an axial plane medical image slice segmented with a spline along the inner surface of the acetabular cup.

FIG. 7 illustrates an example of how each of the MRI image slices 10 is segmented with a spline 120 along the inner surface 40 of the acetabular cup 30. The spline 120 includes control points 122.

As shown in FIGS. 3A and 3B, a MRI locator or reference line 32 is positioned so as to extend across a widest part of the cup 30 at the articular edges 34 of the cup 30. A coronal scan angle, which is indicated by the multiple parallel scan lines 36 in each of the axial and sagittal image slices 10, is set to be perpendicular to each of the axial and sagittal MRI locator lines 32 in the respective axial and sagittal MRI image slices 10 depicted in FIGS. 3A and 3B. Thus, the coronal scan angle is set to be perpendicular to each of the axial and sagittal reference lines 32 that connect the articulate edges 34 in the most representative cross section of the cup 30. The fovea 38 and femoral head 39 can be seen clearly in FIG. 3A. The fovea 38 is the recess or non-spherical area of the cup 30 and is the part of the cup 30 that gives a tactile feel and prevents displacement of the mating surface 232 (shown in FIG. 15) of the shape-match hip guide 240 when the surface 232 is in mating surface contact with the cup 30, as described in the following pages.

Figure 4:
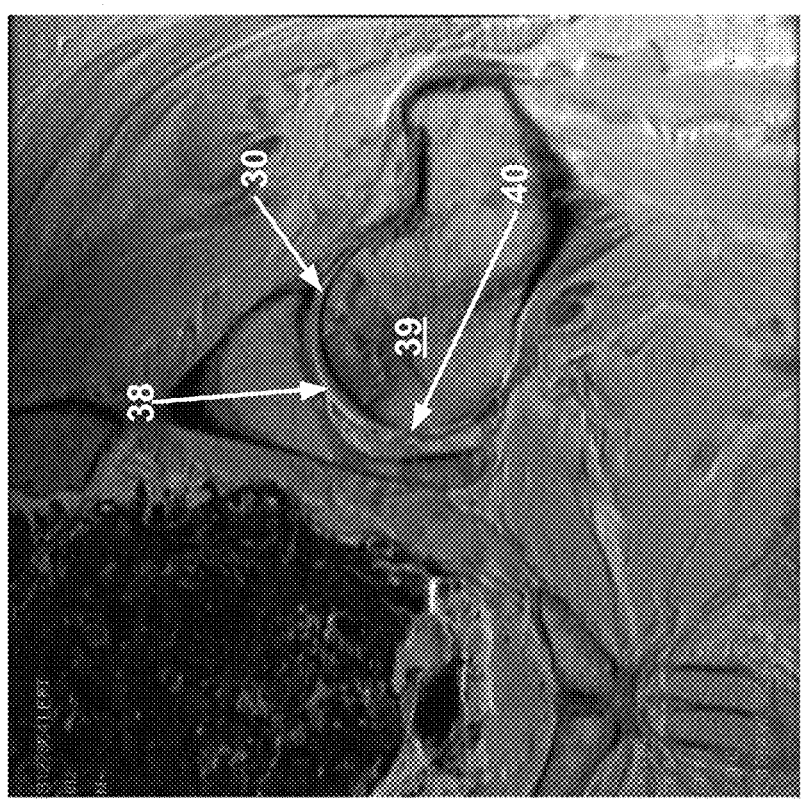
FIG. 4 is an axial plane medical image slice exemplary of the image contrast in the various image slices.

FIG. 4 illustrates a MRI image slice 10 exemplary of the image contrast in the various image slices. The MRI imaging parameters, including TR and TE values are set to make the ideal contrast for the anatomical details of the inner surface 40 of the cup 30 and, especially, the fovea 38.

Figure 5:
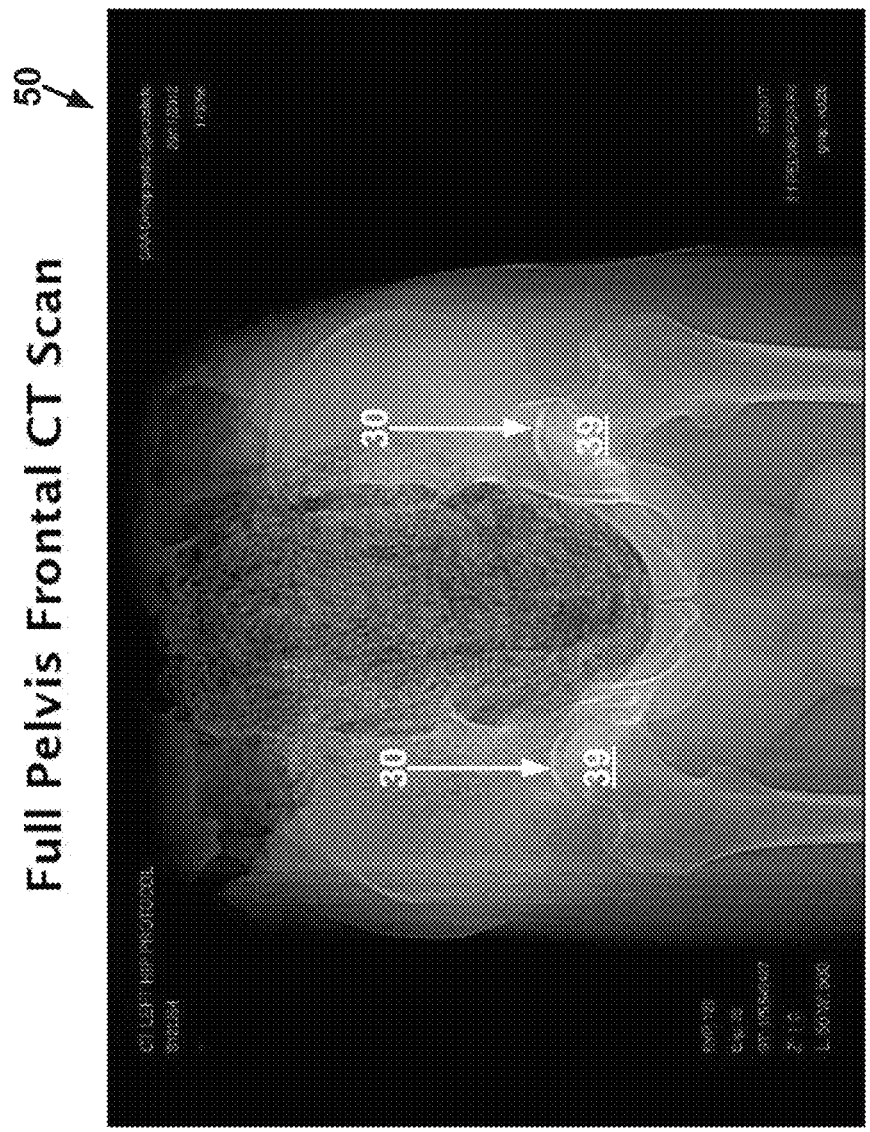
FIG. 5 is a coronal plane medical image slice of the entire hip region used in the preoperative planning stages of a hip replacement procedure.

As indicated in FIG. 1B, landmarks are identified on the 2D medical images [BLOCK 110]. FIG. 5 illustrates a coronal CT image slice 50 of the entire hip area 52 of the patient. This coronal view of the entire hip area 52 is used for preoperative planning, as described as follows. The acetabular cups 30 and the femoral heads 39, along with other useful anatomical landmarks are clearly visible in the CT image slice 50. The landmarks are identified and used to determine a hip axis guide line that will be used in conjunction with the 3D bone model in generating a 3D shape-match hip guide model.

Figure 6A:
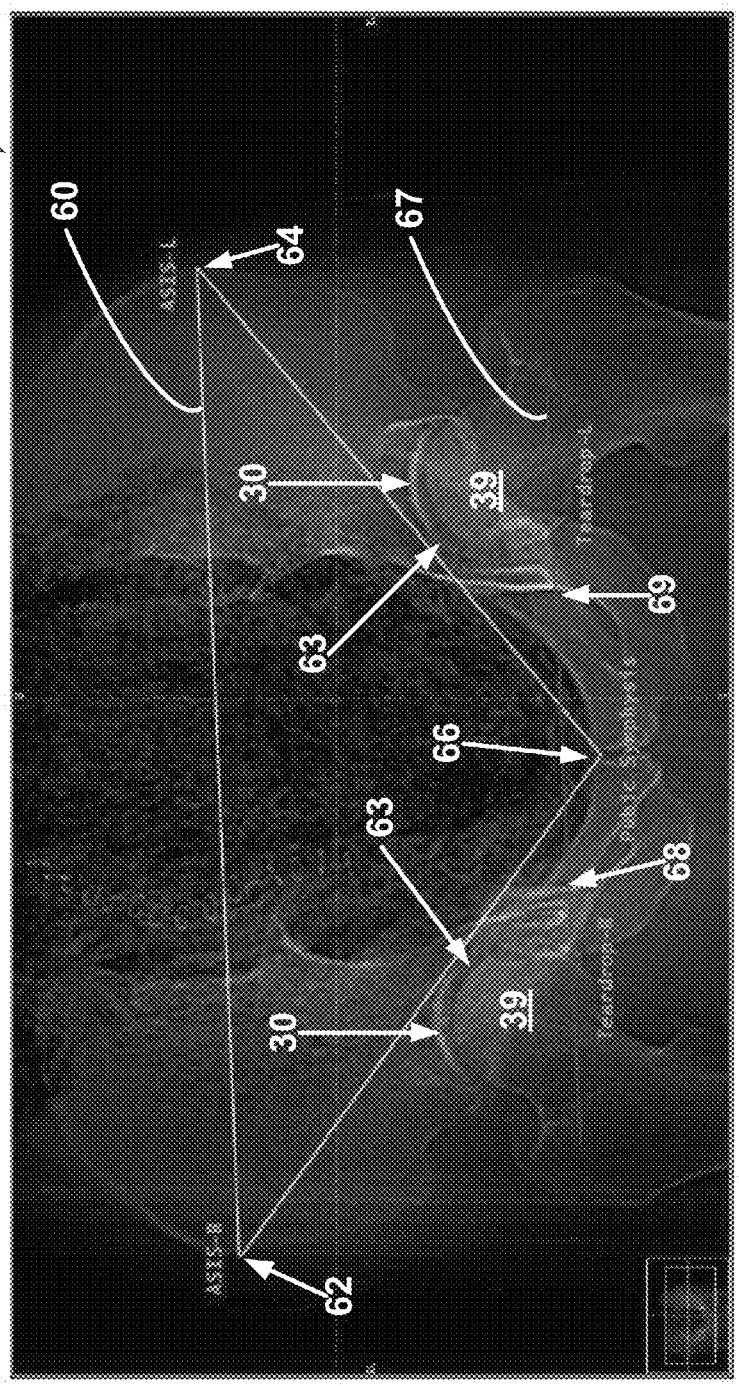
FIGS. 6A-6F are coronal image slices depicting various landmarks and parameters used in the preoperative planning stages of a hip replacement procedure to determine a hip guide pin axis that extends generally along the axis of the femoral head and the femoral neck on the surgical target side of a patient.

FIG. 6A is the same coronal CT image slice 50 of FIG. 5, except a triangle 60 has been defined thereon extending between certain landmarks [BLOCK 115]. Specifically, the preoperative planning methodology begins by defining the triangle 60 across the patient's anterior pelvic area. The triangle's three corners are respectively located at the right anterior-superior ilium symphysis ("ASIS-R") 62, the left anterior-superior ilium symphysis ("ASIS-L") 64, and the pubic symphysis 66. Further, a pelvic axis line 67 is defined to extend across the right teardrop 68 and the left teardrop 69 of the pelvis [BLOCK 120]. Both legs of the triangle 60 (i.e., the sides of the triangle 60 extending between the pubic symphysis and a respective ASIS) can be seen to extend immediately adjacent a proximal point 63 of the acetabular cup 30.

Figure 6B:
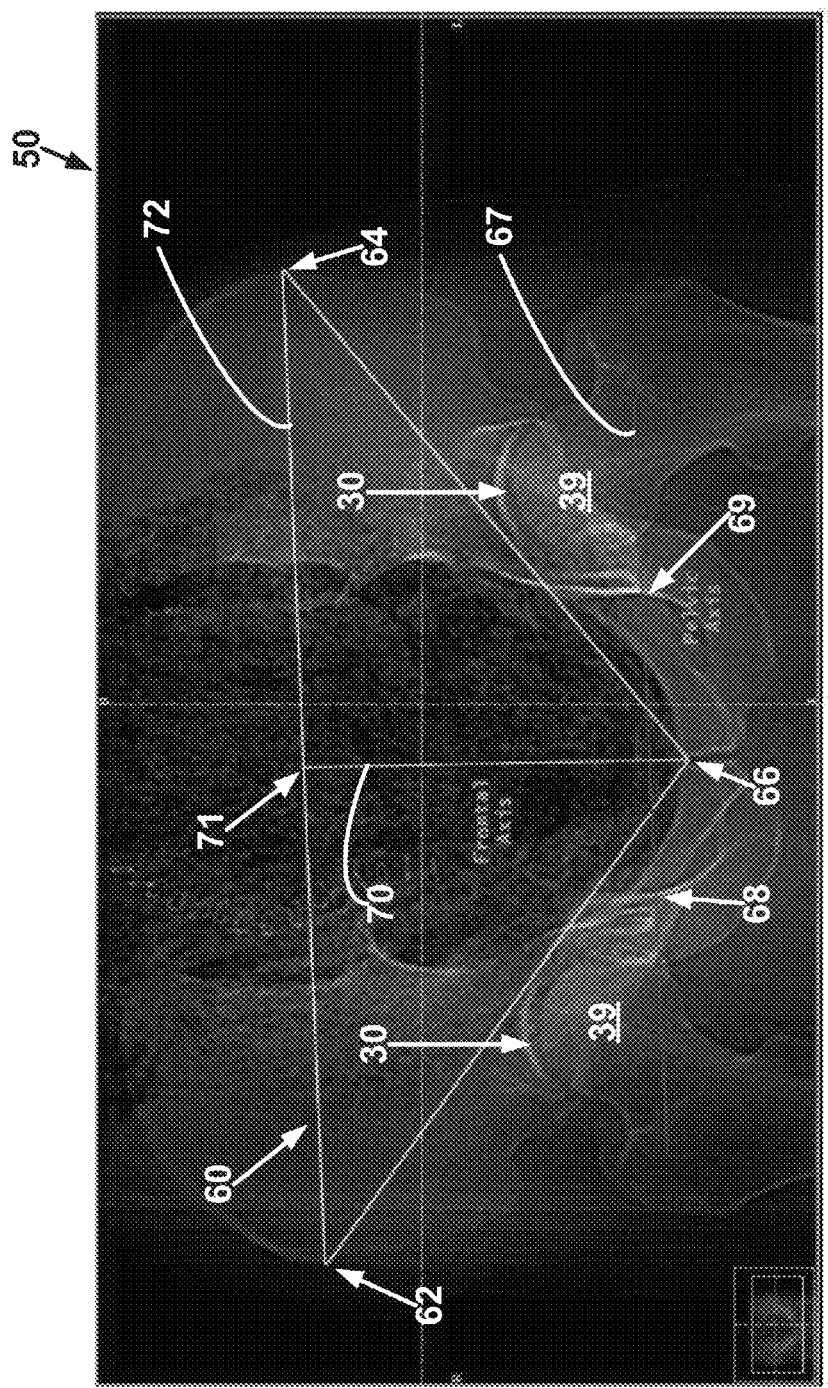

FIG. 6B is the same coronal CT image slice 50 of FIG. 6A, except the triangle 60 has been divided at its height by a frontal axis 70 [BLOCK 125]. As illustrated in FIG. 7, the frontal axis 70 extends between a midpoint 71 of the base line 72 of the triangle 60 that extends between the ASIS-R 62 and ASIS-L 64. The steps of the preoperative planning described with respect to FIGS. 6 and 7 is used to check for pelvic tilt. For example, if the hip joint cartilage is damaged, there will be pelvic tilt such that the pelvic axis 67 and base line (the topmost line) 72 of the triangle 60 will not be substantially parallel.

Figure 6C:
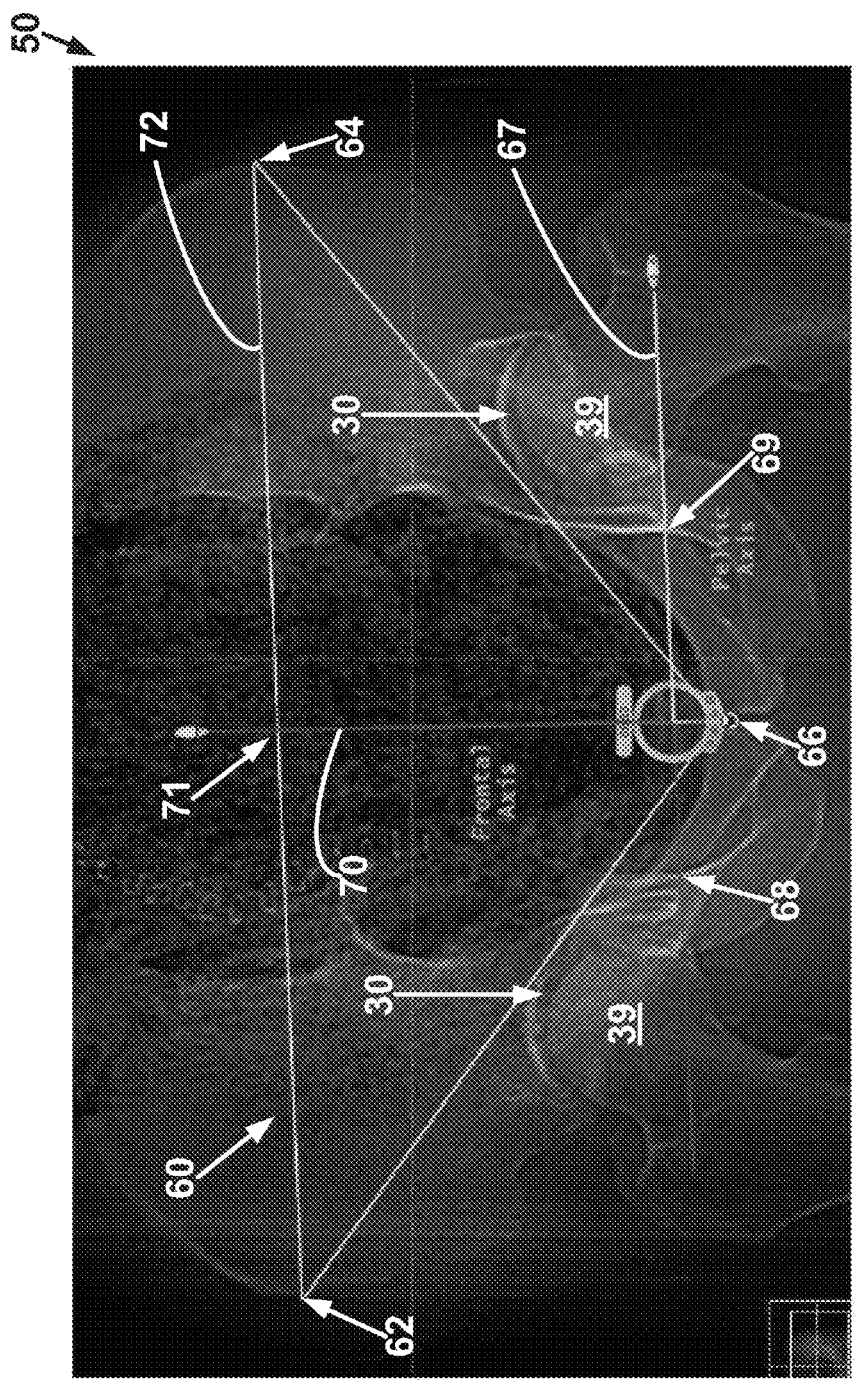

FIG. 6C is the same coronal CT image slice 50 of FIG. 6B, except a check is made to see if the frontal axis 70 and the pelvic axis 67 are perpendicular to each other [BLOCK 130].

Figure 6D:
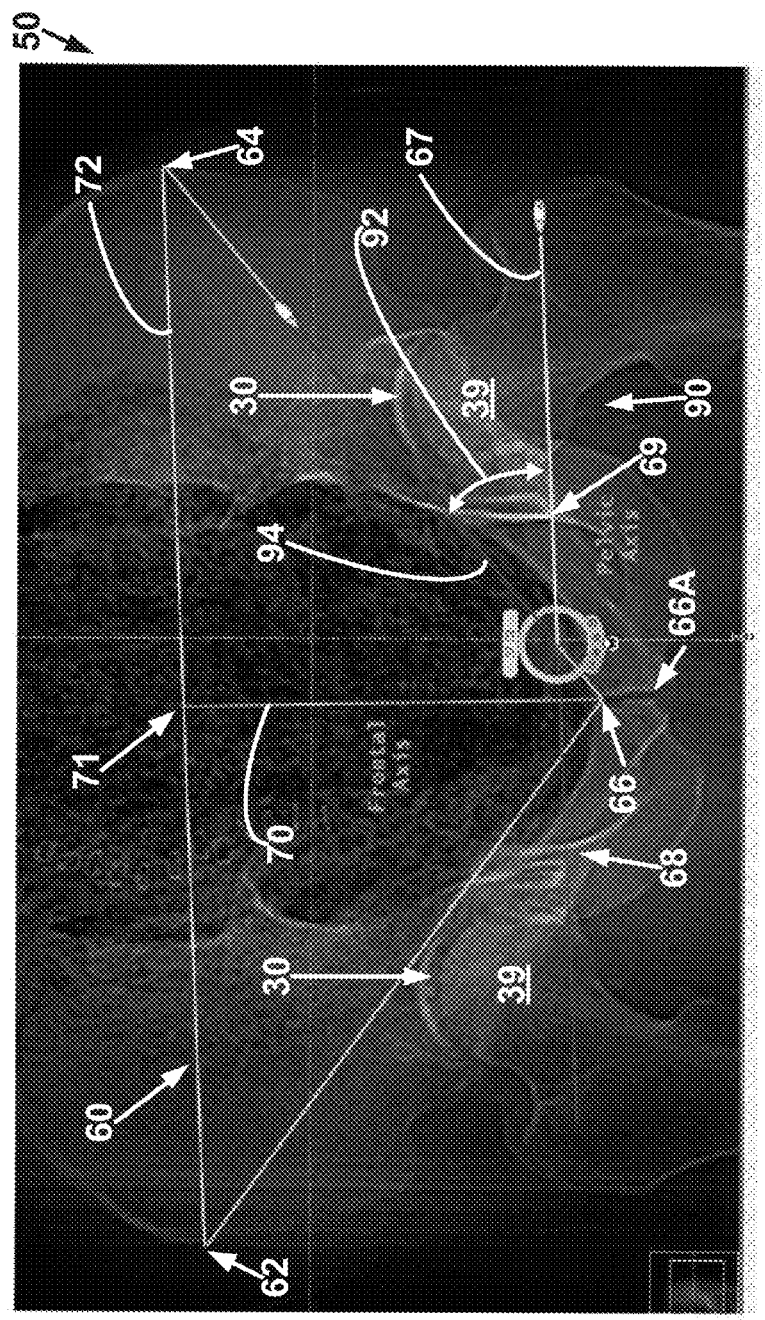

FIG. 6D is the same coronal CT image slice 50 of FIG. 6C, except a measurement is conducted on the patient's surgical target side 90 to determine the angle 92 between the target side line 94 and the pelvic axis 67 [BLOCK 135]. The target side line 94 is the leg of the triangle 60 that extends between the pubic symphysis 66 and the anterior-superior ilium symphysis on the surgical target side 90. Thus, since the surgical target side 90 in the example provided in FIG. 6D is the left side of the patient, the target side line 94 extends between the pubic symphysis 66 and the ASIS-L 64. As indicated in FIG. 6D, the triangle point at the pubic symphysis 66 can be at the superior extent 66 of the pubic symphysis in one embodiment. In other embodiments, the triangle point at the pubic symphysis 66A can be at the inferior extent 66A of the pubic symphysis. In one embodiment, what is considered an appropriate value for the angle 92 in a healthy patient may be a value provided by the surgeon based on the surgeon's examination of the patient and medical images of the patient. In other embodiments, the triangle point at the pubic symphysis 66A can be at the inferior extent 66A of the pubic symphysis. In another embodiment, what is considered an appropriate value for the angle 92 in a healthy patient may be a value provided by medical texts or experts.

Figure 6E:
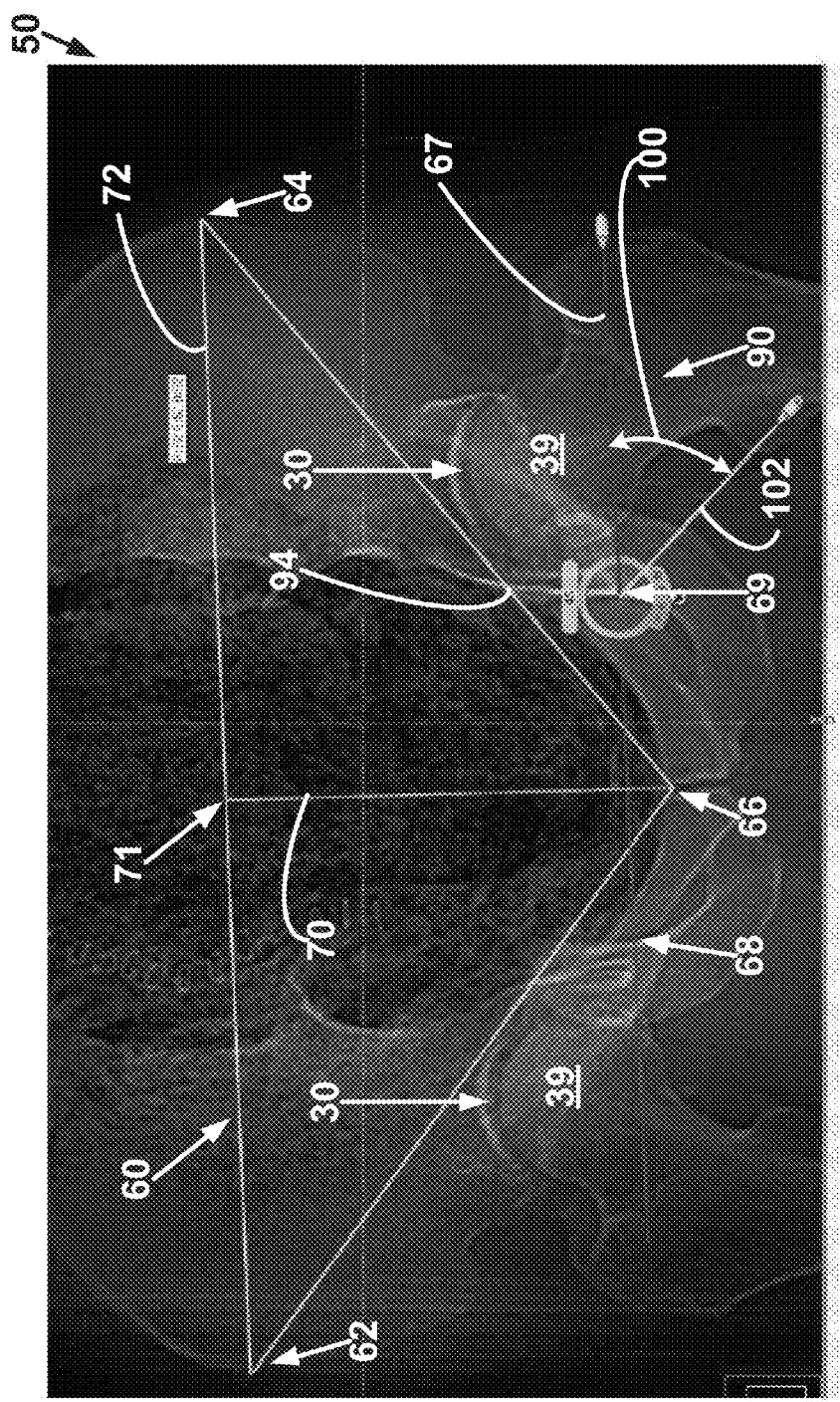

FIG. 6E is the same coronal CT image slice 50 of FIG. 6D, except a 45 degree angle 100 is defined between an axis line 102 and the pelvic axis 67, the intersection of the axis line 100 and the pelvic axis 67 being at the teardrop of the pelvis on the surgical target side 90 [BLOCK 140]. Since the surgical target side 90 is on the patient's left side in this example, the left teardrop 69 is the intersection of the axis line 102 and the pelvic axis 67.

Figure 6F:

FIG. 6F is the same coronal CT image slice 50 of FIG. 6E, except the 45 degree angle 100 has been added to the angle 92 defined in FIG. 6D and the axis line 102 has been moved to intersect the target side line 94 in such a manner that the axis line 102 projects generally along the axis of the femoral head 39 and the femoral neck on the surgical target side 90 [BLOCK 145]. The axis line 102 now generally defines a hip guide pin axis 202 as detailed in the following discussion pertaining to FIGS. 13A and 13B. This hip guide pin axis 202 defines the inclination of the prosthetic acetabular cup 210 as described in the following discussion pertaining to FIGS. 13A and 13B.

II. POP with 3D Bone Model.

Figure 8:
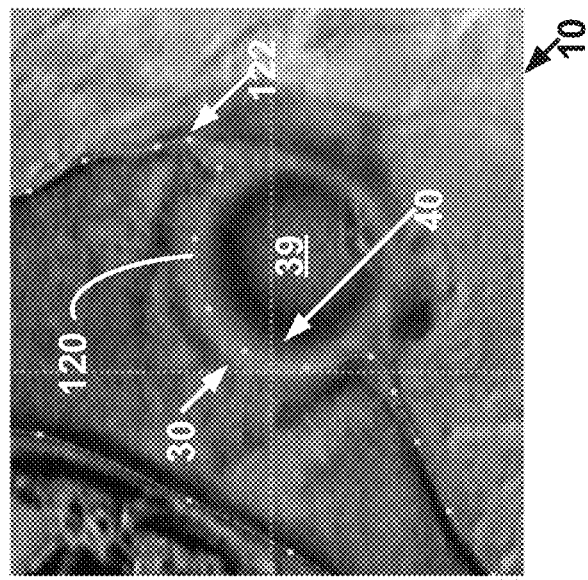
FIG. 8 is another example of a medical image slice segmented with a spline along the inner surface of the acetabular cup.

The 2D medical images can be used to generate a 3D bone model of the area of the patient to undergo an arthroplasty procedure. As shown in FIG. 7, the MRI image slices 10 are segmented with a spline 120 along the inner surface 40 of the acetabular cup 30, wherein the spline 120 includes control points 122. The segmented 2D images and the associated splines 120 and control points 122 are used to generate a 3D bone model. The 3D bone model depicts the bones in the present deteriorated condition with their respective degenerated joint surfaces, which may be a result of osteoarthritis, injury, a combination thereof, etc. FIG. 8 illustrates how the MRI image slices 10 are segmented with a spline 120 that includes control points 122 at the inner surface 40 of the acetabular cup 30, near the anterior and the posterior walls.

Computer programs for creating 3D computer generated bone models from segmented 2D images include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Further, some embodiments may use customized software such as OMSegmentation (renamed "PerForm" in later versions), developed by OtisMed, Inc. The OMSegmentation (or PerForm) software may extensively use "ITK" and/or "VTK" (Visualization Toolkit from Kitware, Inc., available at www.vtk.org). Some embodiments may include using a prototype of OMSegmentation, and such may utilize InsightSNAP software.

Figure 9:
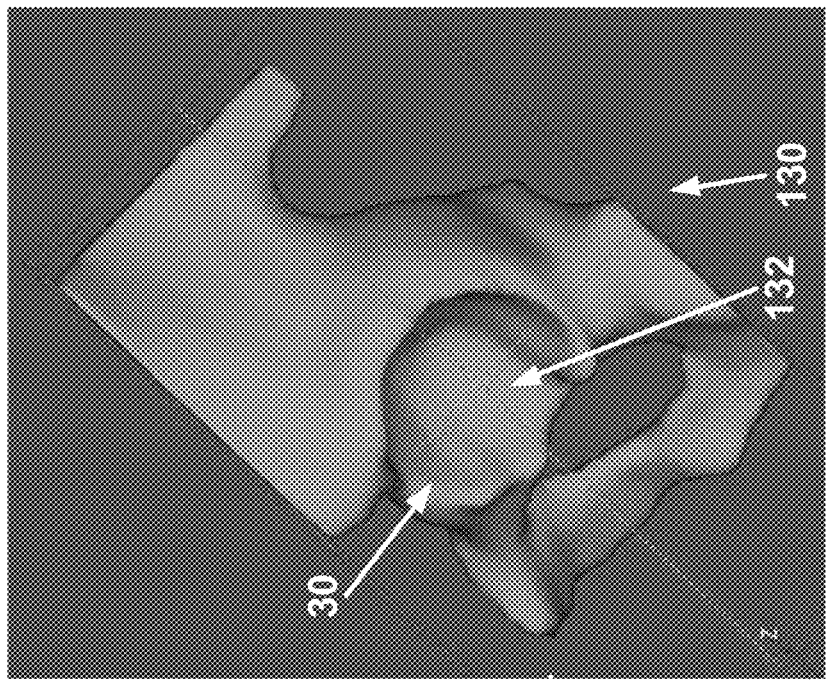
FIG. 9 is a computer generated three dimensional surface model of a patient's acetabular cup compiled from various splines.

As indicated in FIG. 1D, the 3D computer bone models are generated from 2D medical images in the preoperative planning stages of an arthroplasty procedure [BLOCK 150]. FIG. 9 depicts a computer generated three dimensional surface model 130 compiled from the various splines 120. The 3D surface model 130 includes a portion of the pelvis and the contour surface 132 of the acetabular cup 30, the contour surface 132 being a generally identical replication of the inner surface 40 of the patient's acetabular cup 30.

Figure 10:
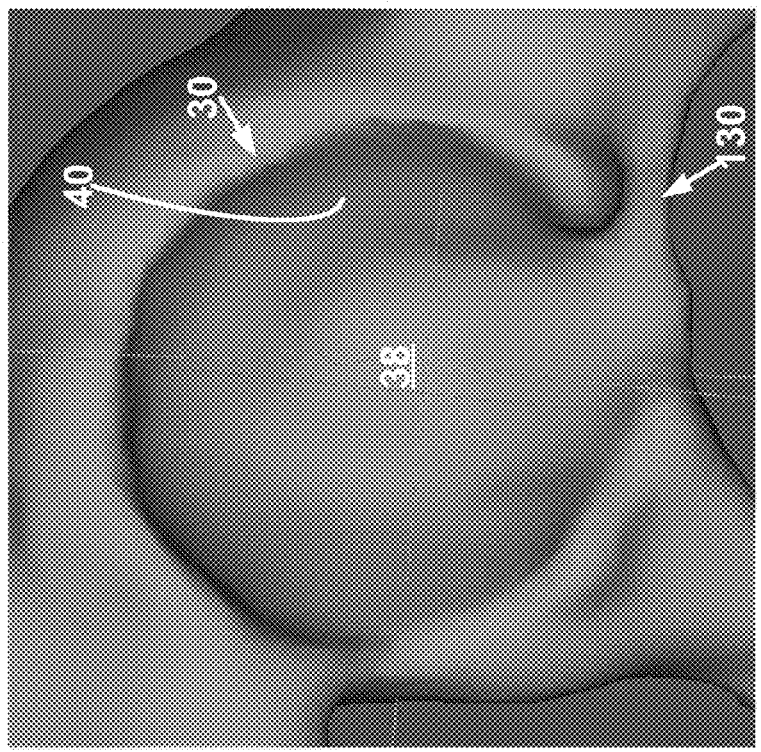
FIG. 10 is an enlarged view of the acetabular cup of the three dimensional model of a patient's acetabular cup.

FIG. 10 is an enlarged view of the acetabular cup 30 of the 3D surface model 130 of FIG. 13, wherein the fovea 38 is more clearly depicted. As already noted, the fovea 38 is the recess or non-spherical area of the inner surface 40 of the cup 30 and is the part of the cup 30 that gives a tactile feel and prevents displacement of the mating surface 232 (shown in FIG. 15) of the shape-match hip guide 252 when the surface 232 is in mating surface contact with the cup 30, as described in the following paragraphs. In one embodiment, the methodology includes checking the surface features of the fovea 38 to see if the trending of the outlines are consistent based on the MRI image analysis.

Figure 11:
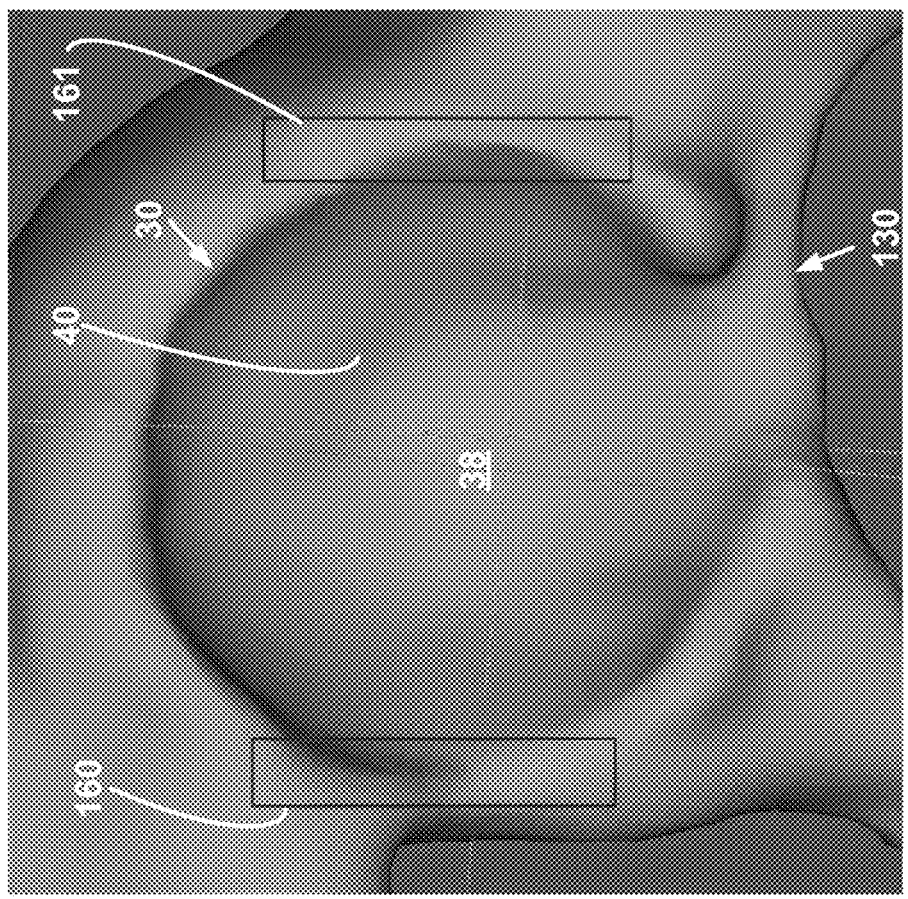
FIG. 11 is an enlarged view of the acetabular cup of the three dimensional model that depicts possible inaccurate areas that form when converting two dimensional medical images into three dimensional models.

As can be understood from FIG. 8, the medical imaging scan angle described in FIGS. 3A and 3B can limit the accuracy of the anterior and posterior wall segmentation. As a result, the corresponding 3D model 130 has inaccuracies in the anterior and posterior regions of the cup 30. These inaccurate areas of the 3D model 130 are enclosed by the rectangles 160, 161 in FIG. 11, which is the same enlarged view of the cup 30 of the 3D model 130 of FIG. 10. These inaccurate areas may be subjected to an "overestimation" process as described in U.S. patent application Ser. No. 12/505,056, filed Jul. 17, 2009 and hereby incorporated by reference in its entirety into the present application. By overestimating the inaccurate areas, the portions of the mating surface 232 of the shape-match hip guide 252 corresponding to the inaccurate areas will not make surface contact the patient's cup inner surface corresponding to the inaccurate regions when the mating surface 232 matingly engages other portions of the patient's inner cup surface [BLOCK 155].

Figure 12A:
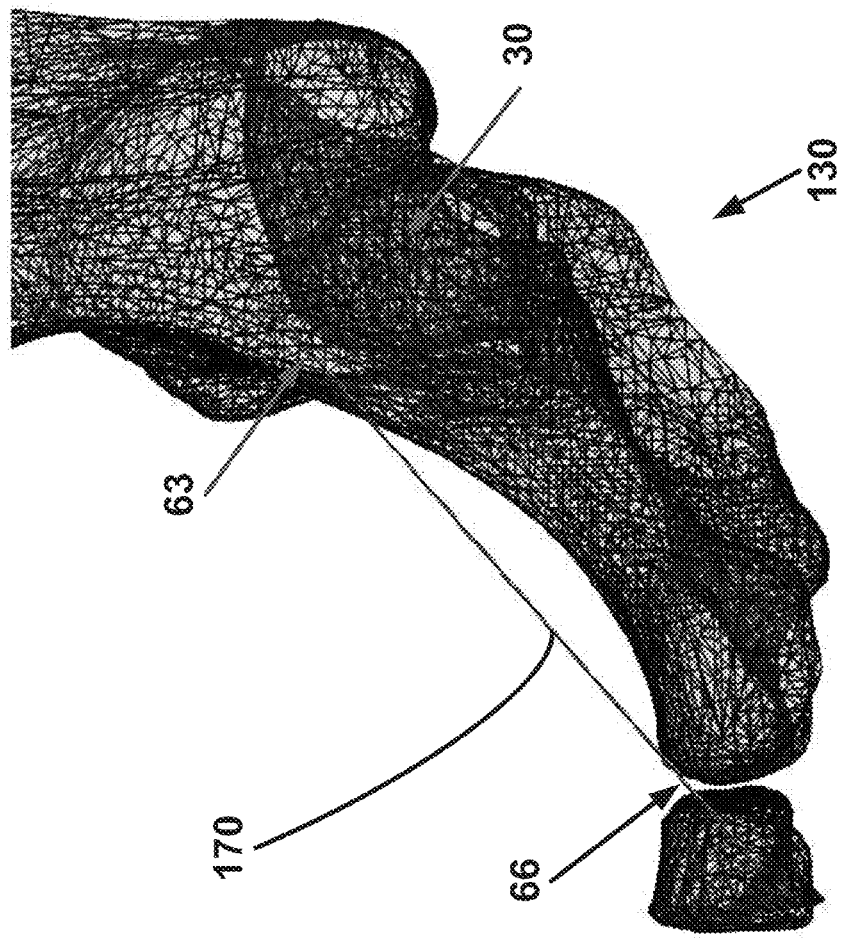
FIGS. 12A-12D are three dimensional surface models of a patient's acetabular cup in a coronal plane, with similar landmarks and parameters employed in FIGS. 6A-6F in determining a hip guide pin axis that extends generally along the axis of the femoral head and the femoral neck on the surgical target side of a patient.

FIG. 12A is the 3D surface model 130 of FIG. 9 shown in the same coronal view used in FIGS. 6A-6F. The planning process explained with respect to the coronal CT scan 50 of FIGS. 6A-6F will now be replicated with respect to the 3D model 130. Thus, as shown in FIG. 12A, a plane 170 connects the proximal point of the pubic symphysis 66 with a proximal point 63 of the acetabular cup 30 [BLOCK 165]. Thus, the plane extends from the pubic symphysis 66 to a point 63 near the fovea, thereby replicating the geometry of the planning step described with respect to FIG. 6A.

Figure 12B:
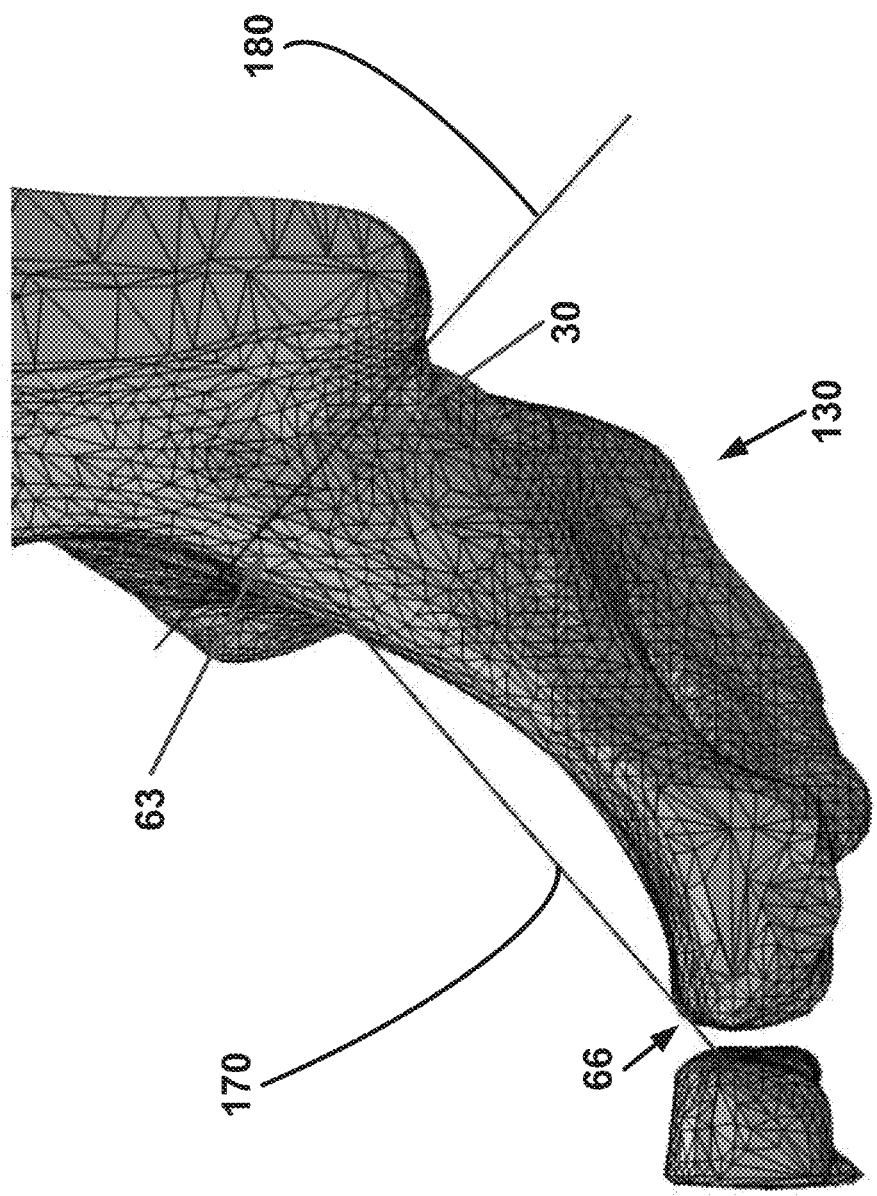

FIG. 12B is the 3D surface model 130 of FIG. 12A further along in the planning process replication. As shown in FIG. 12B, a second plane 180 is provided such that the second plane 180 intersects the first plane 170 at the proximal point 63 of the acetabular cup 30 [BLOCK 170]. Thus, the second plane 180 is oriented to mimic the trajectory of the axis 102 of FIG. 6F, thereby replicating the geometry of the planning step described with respect to FIG. 6F.

Figure 12C:
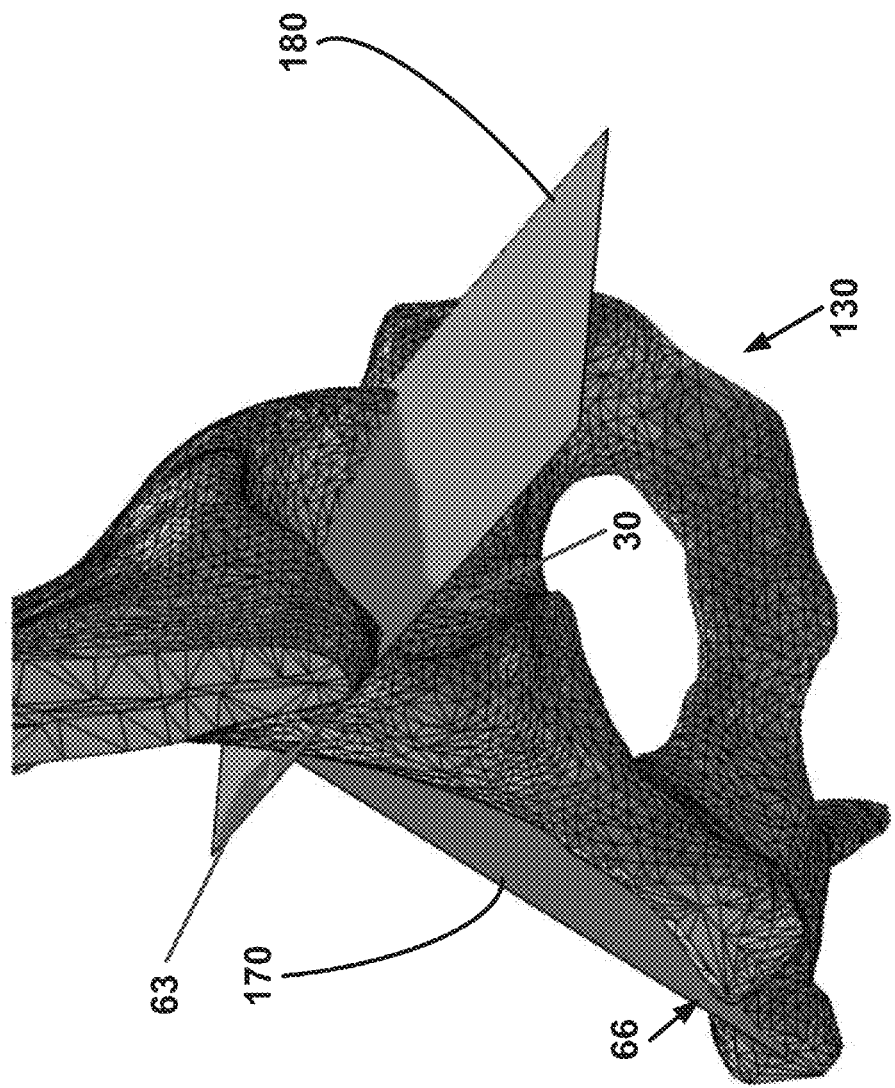

FIG. 12C is the 3D surface model 130 of FIG. 12B with the same planes 170, 180, but rotated so as to show the model 130 from a more inferior and lateral perspective. As illustrated in FIG. 12C, the second plane 180, which may be called an inclination plane 180, extends through the center point of the acetabular cup 30. In one embodiment, the view of the model 130 provided in FIG. 12C may be considered perpendicular to the coronal view depicted in FIG. 12B.

Figure 12D:
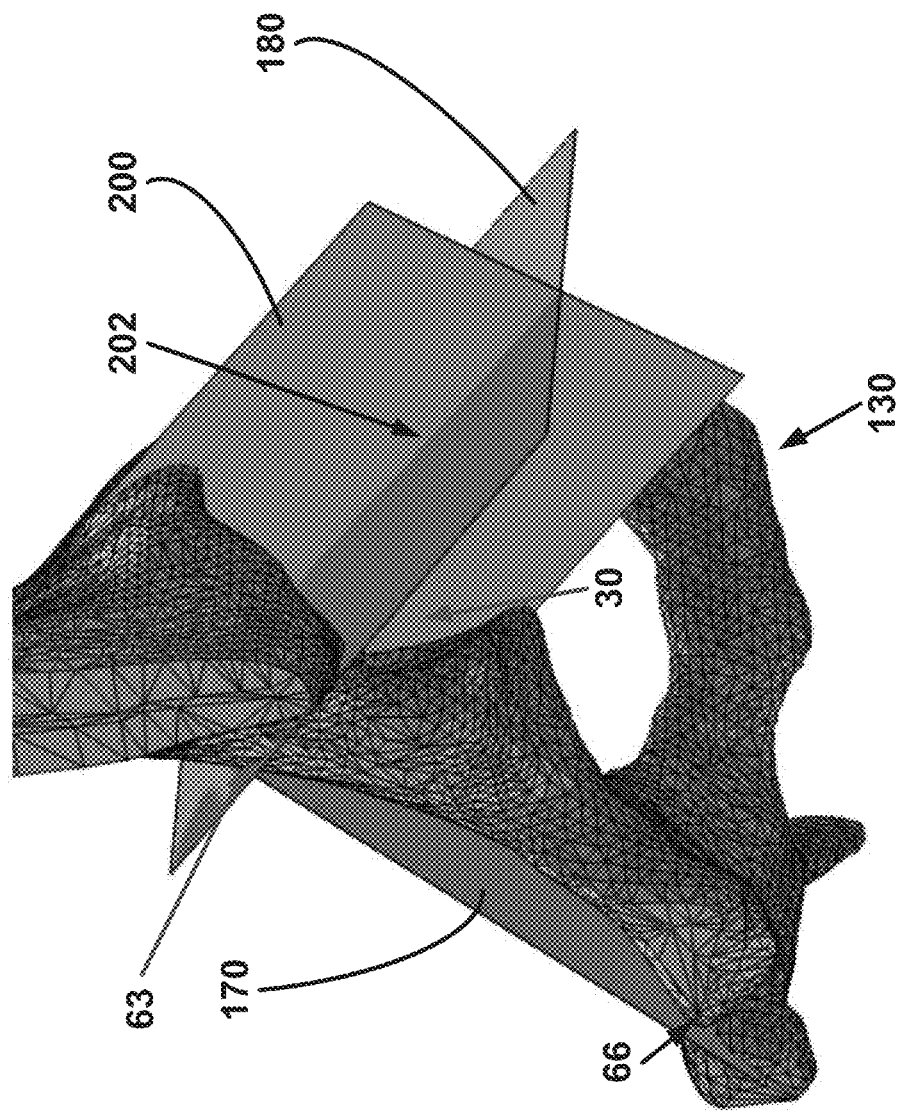

FIG. 12D is the 3D surface model 130 of FIG. 12C with the same planes 170, 180 and further including a third plane 200, which may be called the anteversion plane 200 [BLOCK 175]. As illustrated in FIG. 12D, the anteversion plane 200 is positioned to evenly divide the anterior and posterior walls of the acetabular cup 30 and also pass through the center of the acetabular cup 30. The anteversion plane 200 is perpendicular to the 45 degree line plane (i.e., the inclination plane 180). Also, the anteversion plane 200 divides the inclination plane 180 in half. The intersection of the two planes 180, 200 defines an axis line 202 that approximates a center axis of the acetabular cup 30.

FIG. 13A illustrates the 3D surface model 130 of FIG. 12D further rotated with the same planes 170, 180, 190 and further including a 3D model of a candidate prosthetic acetabular cup 210 occupying the acetabular cup 30 of the 3D surface model 130 [BLOCK 180]. The prosthetic cup 210 is positioned relative to the inclination and anteversion planes 180, 200 such that a center axis of the cup is coaxial with the axis 202 defined by the intersection of the planes 180, 200. Thus, the placement of the 3D model of the prosthetic cup 210 in the cup 30 of the 3D surface model 130 relative to the axis 202 results in the preoperative planning of the surgical placement of an actual prosthetic acetabular cup in the actual acetabular cup of the patient.

Figure 13B:
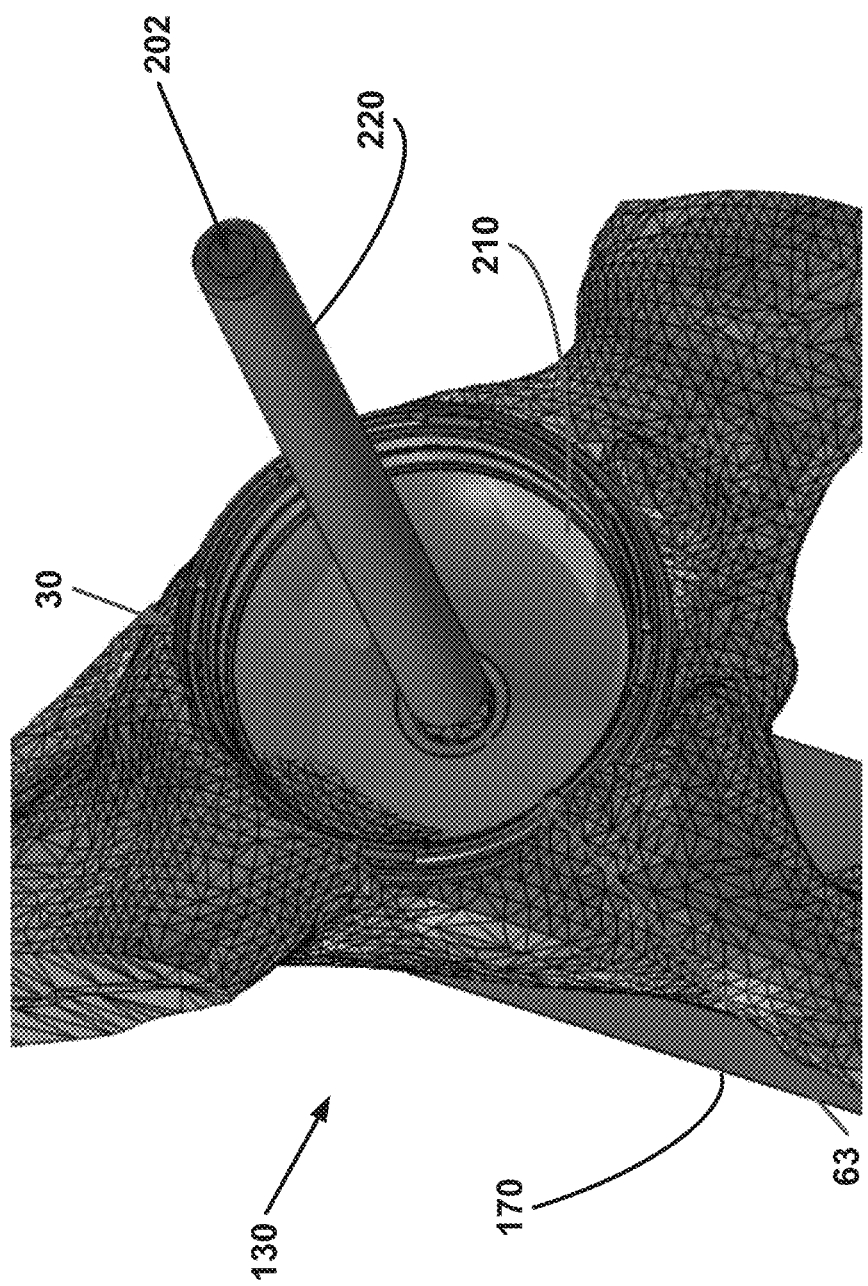

FIG. 13B illustrates the 3D surface model 130 of FIG. 13A wherein the planes 180, 190 have been removed and a 3D model of a directional rod 220 has been coupled to the interior surface of the 3D model of the candidate prosthetic acetabular cup 210 occupying the acetabular cup 30 of the 3D surface model 130. The directional rod 220 is positioned so as to be coaxial with the axis 202 defined by the intersection of the planes 180, 200 in FIG. 13A. Thus, the placement of the 3D model of the directional rod 220 to be coaxial with the axis 202 defined by the intersection of the planes 180, 200 in FIG. 13A replicates the inclination angle from the preoperative planning depicted in FIG. 6F.

Figure 14:
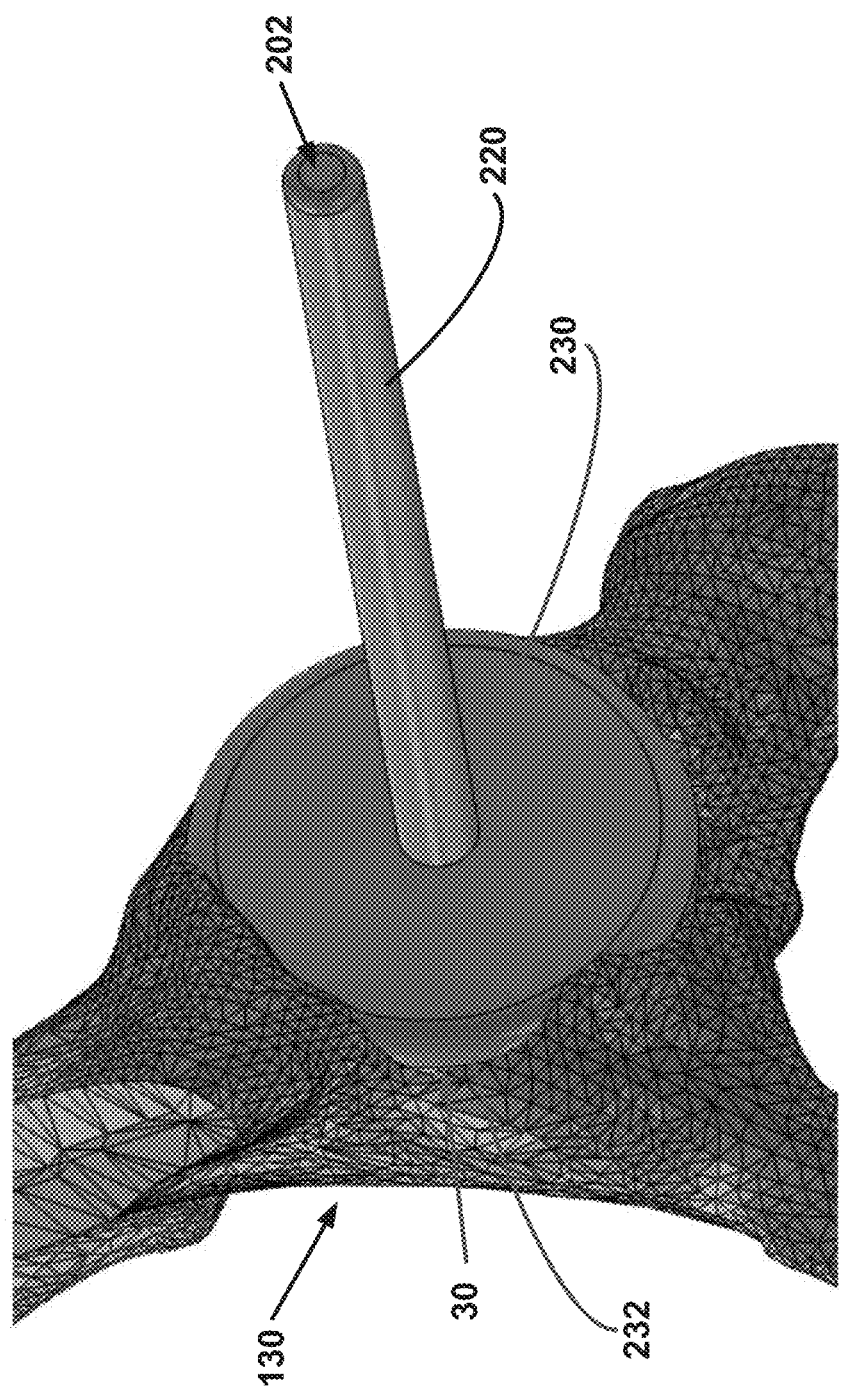
FIG. 14 is a three dimensional surface model of a patient's acetabular cup, similar to FIG. 13, wherein the candidate prosthetic acetabular cup is replaced in the acetabular cup of the 3D surface model by a 3D model of a semi-hemispherical blank or mold.

FIG. 14 illustrates the 3D surface model 130 of FIG. 13B wherein all the planes 170, 180, 190 have been removed, the 3D model of the directional rod 220 is still coaxially positioned relative to the axis 202 as described with respect to FIG. 13B and the 3D model of the candidate prosthetic acetabular cup 210 has been replaced in the acetabular cup 30 of the 3D surface model 130 by a 3D model of a semi-hemispherical blank or mold 230 [BLOCK 185]. The hemispherical surface 232 of the semi-hemispherical blank or mold 230 extends along the surface contour of the inside surface of the acetabular cup 30 of the 3D surface model 130. As a result, the hemispherical surface 232 of the semi-hemispherical blank or mold 230 is caused to assume a surface contour that is a negative of the surface contour of the inside surface of the acetabular cup 30 of the 3D surface model 130.

FIG. 15 illustrates the completed 3D model of a shape-match hip guide 240 including the directional rod 220 extending from the semi-hemispherical blank or mold 230, which has the hemispherical surface 232 that is a negative of the surface contour of the inside surface of the acetabular cup 30 of the 3D surface model 130. Thus, when an actual shape-match hip guide 252 is manufactured to match the model guide 240, the shape-match hemispherical surface of the actual hip guide 252 will matingly interdigitate with the corresponding inner surface of the patient's acetabular cup and cause the directional rod 220 to be extend along a directional line that mimics the axis 202 preoperatively planned according to the steps outlined in FIGS. 6A-6F and 12A-14.

As illustrated in FIG. 1E, the 3D model shape-match hip guide 240 is sent to a CNC machine 13 or other suitable prototyping machine in order to machine or produce a physical shape-match hip guide 252 [BLOCK 195-200]. Data associated with the 3D model shape-match hip guide 240 can be transferred to a storage medium (e.g., compact disc, digital video disc, flash drive) and physically delivered to a manufacturer or the data can be electronically sent via a network connection to a manufacturer. Alternatively, the computer that generates the 3D model shape-match hip guide 240 can be directly connected to a CNC machine 13 for machining of the physical shape-match guide 252. The mating surface 232 of the hip guide 252 can be machined by an additive process, such as by a rapid prototyping machine, or by a reductive process, such as by machining in a CNC machine 13. In the case of a machining process in a CNC machine 13 or similar device, a guide blank 51 will be inputted into the CNC machine 13 and the machine will generate the customized mating surface 232 of the blank or mold 51.

In one embodiment, the POP procedure is a manual process, wherein computer generated 3D bone models are manually manipulated by a person sitting in front of a computer and visually observing the bone model and the generation of the model shape-match hip guide 240 via the computer controls. In one embodiment, the bone modeling process is generally or completely automated. In other words, a computer program may analyze the bone models and their degenerated surface to determine the steps involved in the preoperative planning process of the procedure (e.g., a computer may perform the "overestimation" process and generate an appropriate bone model).

III. Operating Procedure.

Once the POP phase of the procedure is complete and a physical shape-match guide 252 is generated, a surgeon can perform the arthroplasty procedure with the shape-match guide 252.

A. Employing the Shape-Match Hip Guide.

A first embodiment of a method of employing the guide 252 will now be discussed. In preparation for the arthroplasty procedure, the region of a patient's body to undergo the procedure is prepared for surgery [BLOCK 205]. The preparation can include a surgeon or a surgical assistant making the appropriate incisions into the target area of the patient's body 12. Once the target area 12 is accessible for the procedure, the actual shape-match hip guide 252 is matingly received in the patient's acetabular cup [BLOCK 210]. FIGS. 16A and 16B are inferior-lateral views of a patient's actual hip region 250 including the surgical target acetabular cup 251 in the process of receiving an actual prosthetic acetabular cup 260. As shown in FIG. 16A, an actual shape-match hip guide 252 is matingly received in the acetabular cup 251. The hip guide 252 includes a directional rod 253 extending from a semi-hemispherical head 254 having a hemispherical surface that is a surface negative of the surface contour of the inside surface of the surgical target acetabular cup 251. The guide 252 is manufactured to be generally an exact physical replica of the preoperatively planned 3D model guide 240 of FIG. 15.

As can be understood from FIGS. 16A and 16B, the mating surface of the head 254 of the guide 252 is interdigitated with the inner surface of the acetabular cup 251 to matingly engage with the inner surface such that the rod 253 extends from the cup 251 as preoperatively planned and discussed with respect to FIG. 15. The surgeon estimates the orientation of the rod 253 as depicted in FIG. 16A and then removes the guide 252 from the cup 251 [BLOCK 215]. The surgeon then reams the acetabular cup 251 [BLOCK 220]. The surgeon tries to replicate the same orientation of the rod 253 shown in FIG. 16A with the reamer [BLOCK 225].

As can be understood from FIG. 16B, once the reaming is complete, the surgeon then inserts the prosthetic cup 260 into the acetabular cup 251 via an impactor shaft 262 supporting the cup 260 [BLOCK 230]. While using the shaft 262 to drive the prosthetic cup 260 into the acetabular cup 251, the surgeon tries to replicate the same orientation of the rod 253 shown in FIG. 16A with the impactor rod 262 used in FIG. 16B [BLOCK 235]. The surgeon then removes the impactor from the target area [BLOCK 236].

B. Employing the Shape-Match Hip Guide with an Outrigger Alignment Device.

Figures 17A, 17B:
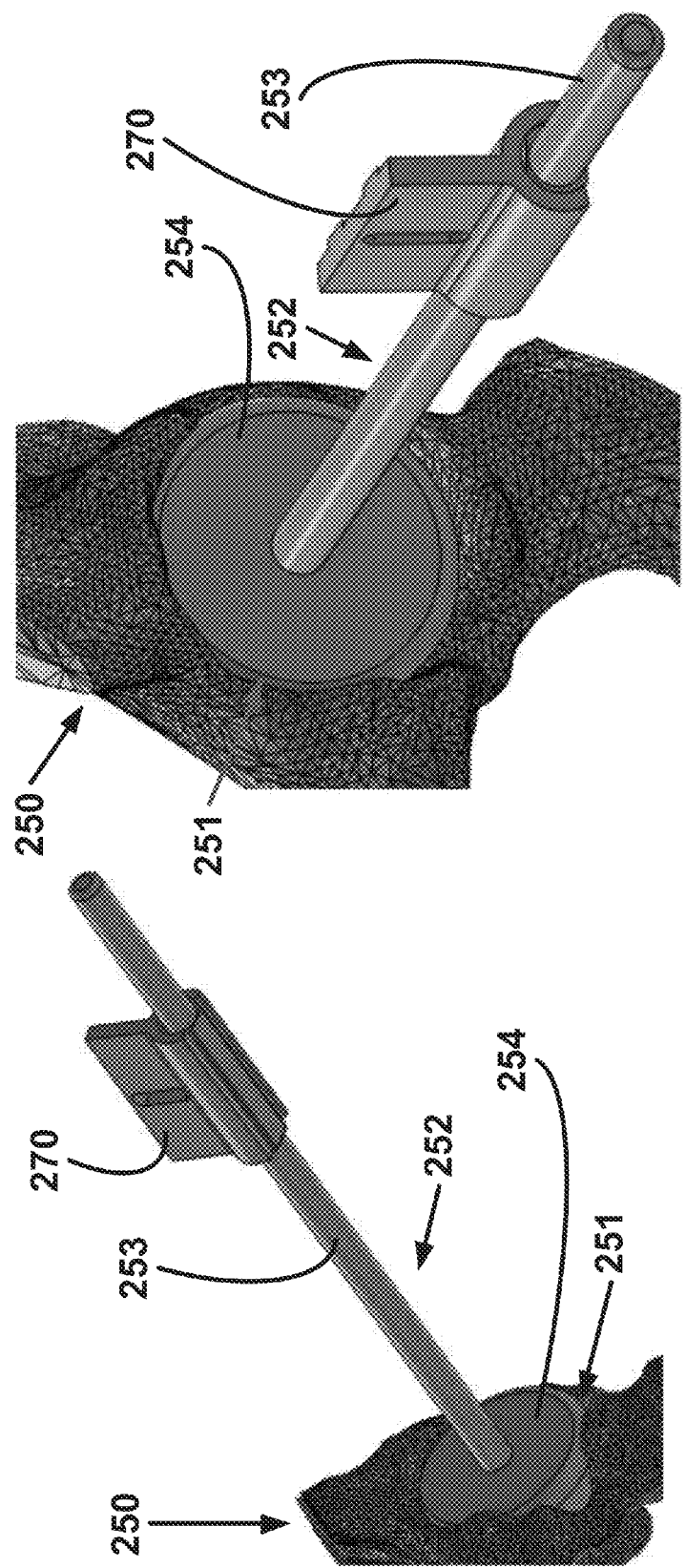
FIGS. 17A-17G are views of a patient's actual hip region including the acetabular cup in the process of receiving an actual prosthetic acetabular cup via a shape-match hip guide and an outrigger device used in aligning the reaming of the patient's acetabular cup and/or implantation of a prosthetic acetabular cup.

A second embodiment of a method employing the guide 252 will now be discussed. In preparation for the arthroplasty procedure, the region of a patient's body to undergo the procedure is prepared for surgery [BLOCK 240]. The preparation can include a surgeon making the appropriate incisions into the target area of the patient's body. Once the target area is accessible for the procedure, the actual shape-match hip guide 252 is matingly received in the patient's acetabular cup [BLOCK 245]. FIGS. 17A and 17B are views of the patient's actual hip region 250 including the surgical target acetabular cup 251 in the process of receiving an actual prosthetic acetabular cup via another method in conjunction with an outrigger device for employing the actual shape-match hip guide 252. As shown in FIGS. 17A and 17B, the actual shape-match hip guide 252 is matingly received in the acetabular cup 251 as described with respect to FIG. 16A, and a first coupler half 270 of the outrigger device extends over the rod 253.

Figures 17C, 17D:
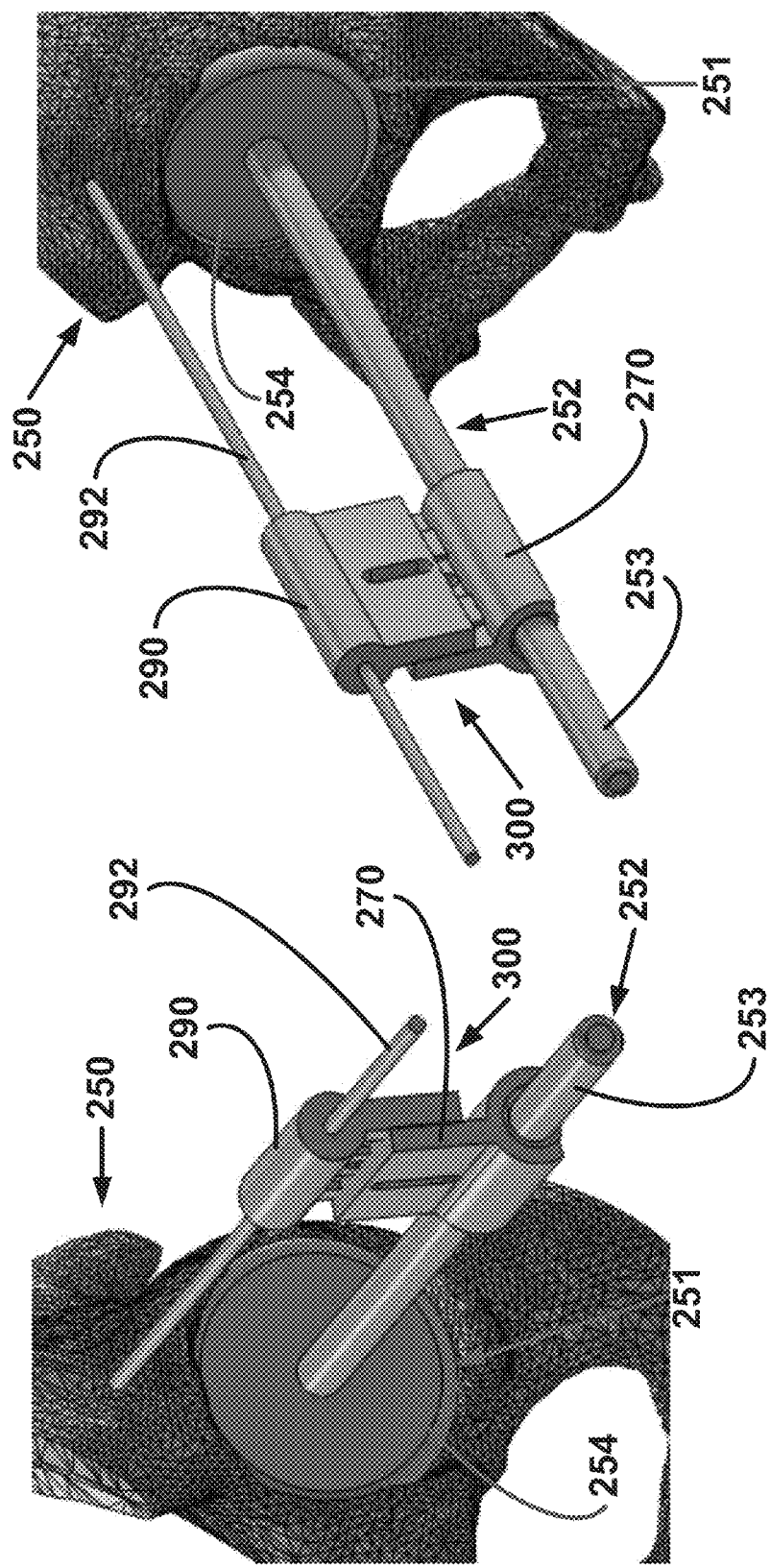

FIGS. 17C and 17D are views of the patient's actual hip region 250 further illustrating the process of employing the outrigger device 300 with the shape-match hip guide 252. As shown in FIGS. 17C and 17D, a second coupler half 290 is coupled to the first coupler half 270, and a reference rod 292 extends through the second coupler half 290 to be imbedded in the bone of the superior hip region 250 [BLOCK 250-255]. The first and second coupler halves 270, 290 and the reference rod 292 are the major components of the outrigger device 300. The reference rod 292 is held parallel to the rod 253 of the guide 252 by the outrigger device 300 [BLOCK 255].

Figure 17E:
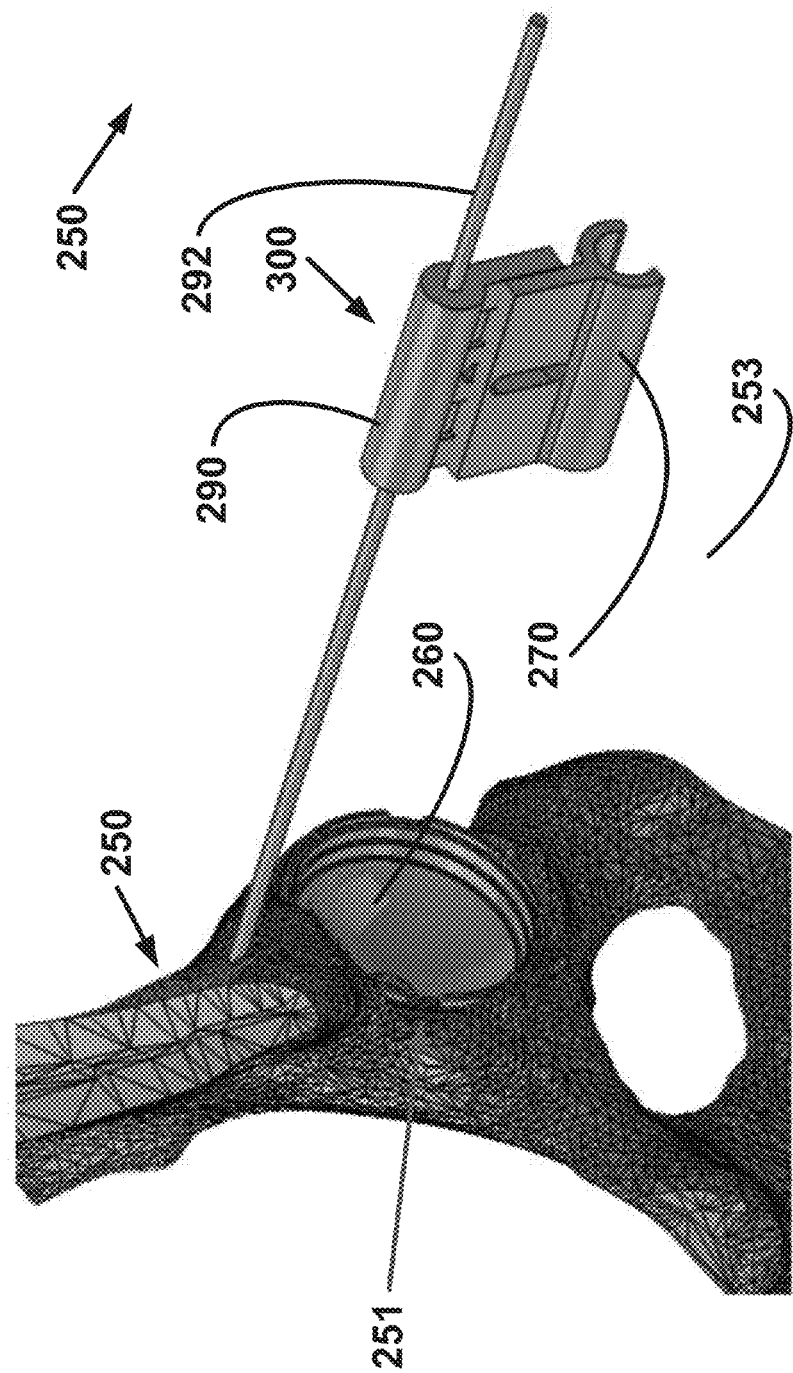

FIG. 17E is a view of the patient's actual hip region 250 further illustrating the process of employing the outrigger device 300 with the shape-match hip guide 252. As shown in FIG. 17E, the hip guide 252 is removed from the acetabular cup 251 and the outrigger device 300 while maintaining the outrigger device 300 in the same orientation and location shown in FIG. 17E via the reference rod 292 being imbedded in the bone of the patient's hip region 250 [BLOCK 260]. Subsequent to reaming the acetabular cup 251 wherein the reaming angle of the reamer may be guided by the coupler 270, the prosthetic acetabular cup 260 is then placed in the patient's acetabular cup 251 [BLOCK 265-270]. The outrigger device 300 only provides one angle (i.e., the inclination angle), the surgeon having to determine the other angle (i.e., the anteversion angle).

Figure 17F:
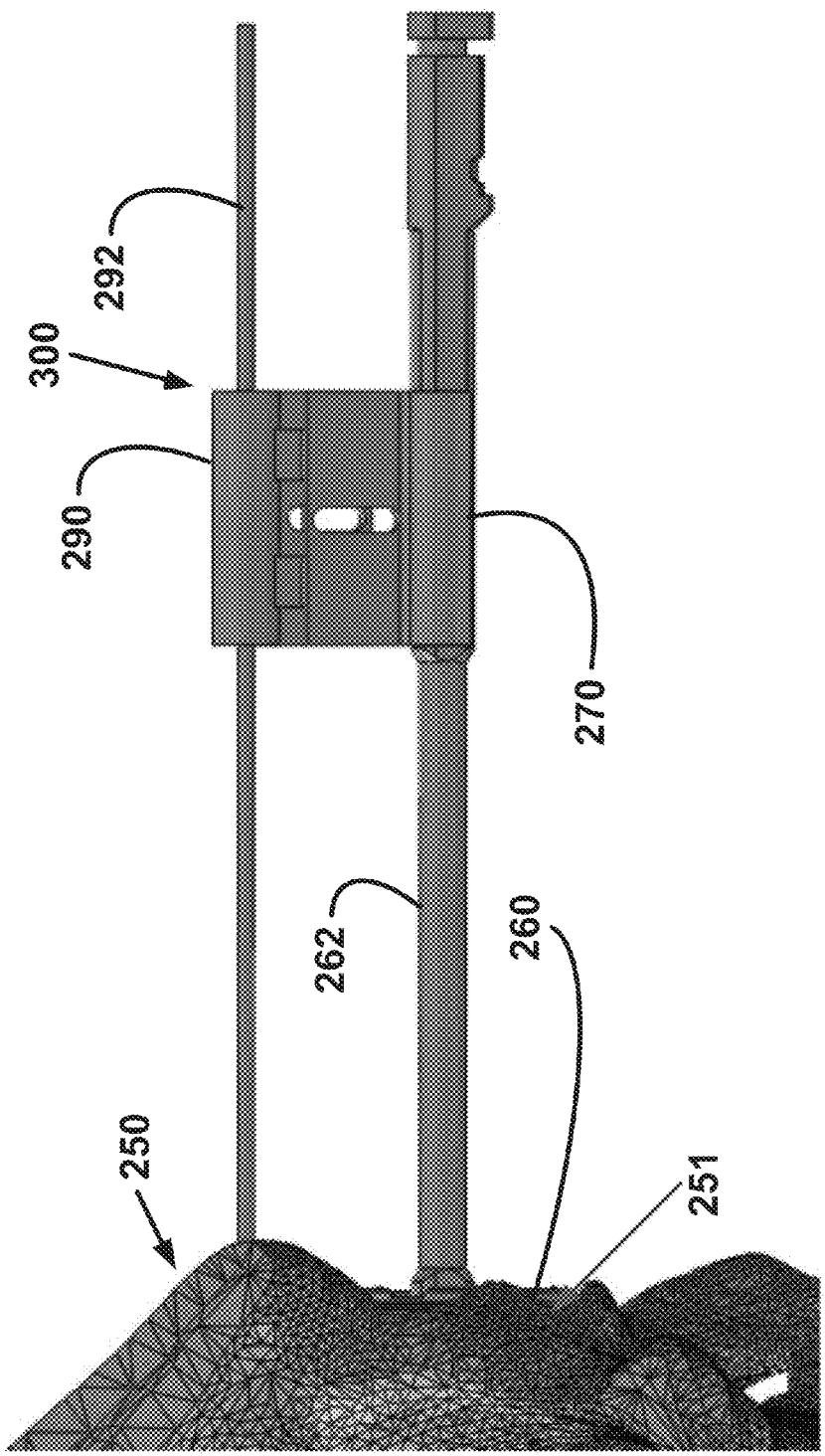

FIG. 17F is a view of the patient's actual hip region 250 further illustrating the process of employing the outrigger device 300 with the shape-match hip guide 252. As shown in FIG. 17F, the impactor rod 262 is placed against the inside of the prosthetic cup 260 and received in the first coupler half 270 previous occupied by the rod 253 of the hip guide 252 as discussed with respect to FIGS. 17A and 17B [BLOCK 275]. The outrigger device 300 maintains the impactor rod 262 in the same orientation and location of the rod 253 of the hip guide 252 on account of the reference rod 292 being imbedded in the bone of the patient's hip region 250. As already noted, the outrigger device 300 only provides one angle (i.e., the inclination angle), the surgeon having to eyeball the other angle (i.e., the anteversion angle).

Figure 17G:
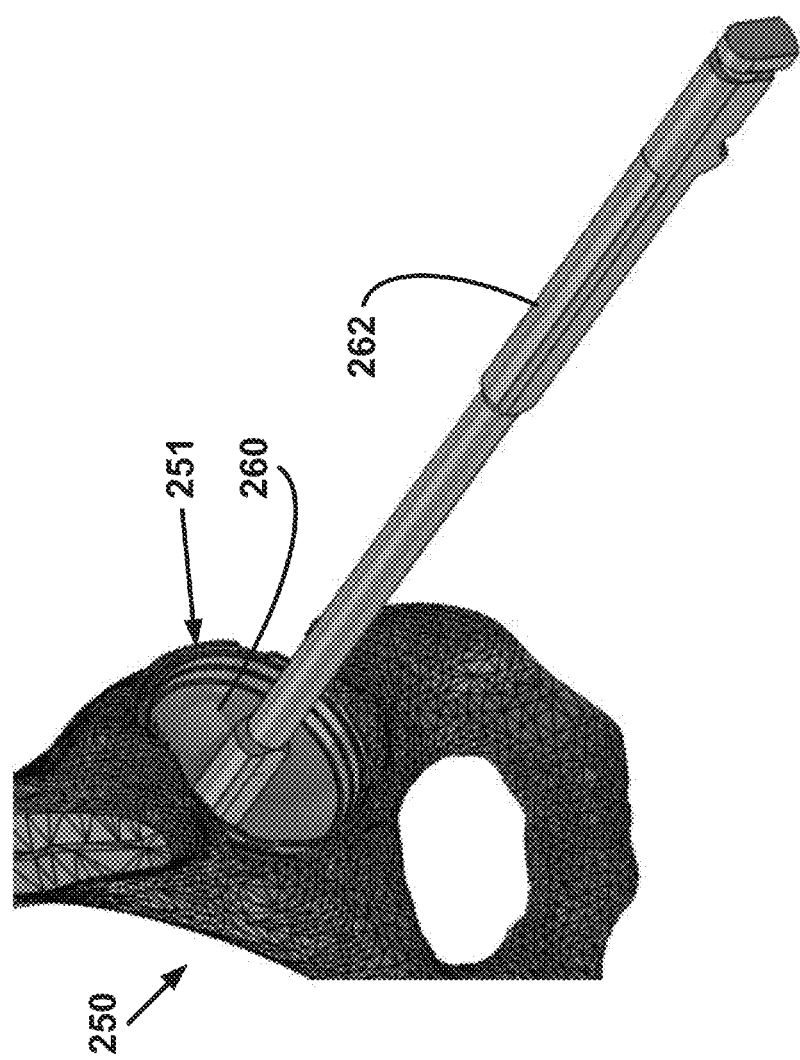

FIG. 17G is a view of the patient's actual hip region 250 illustrating the impactor rod 262 ready for impaction of the prosthetic cup 260 into the patient's acetabular cup 251 after removal of the outrigger device 300 from the impactor rod 262 after the outrigger device 300 was used to align the impactor rod 262 as described with respect to FIG. 17F. The prosthetic acetabular cup is impacted into the patient's acetabular cup [BLOCK 280]. Following impaction, the impactor and outrigger device are removed from the patient's acetabulum [BLOCK 281].

C. Employing the Shape-Match Hip Guide with a Silo Alignment Device.

Figures 18A, 18B:
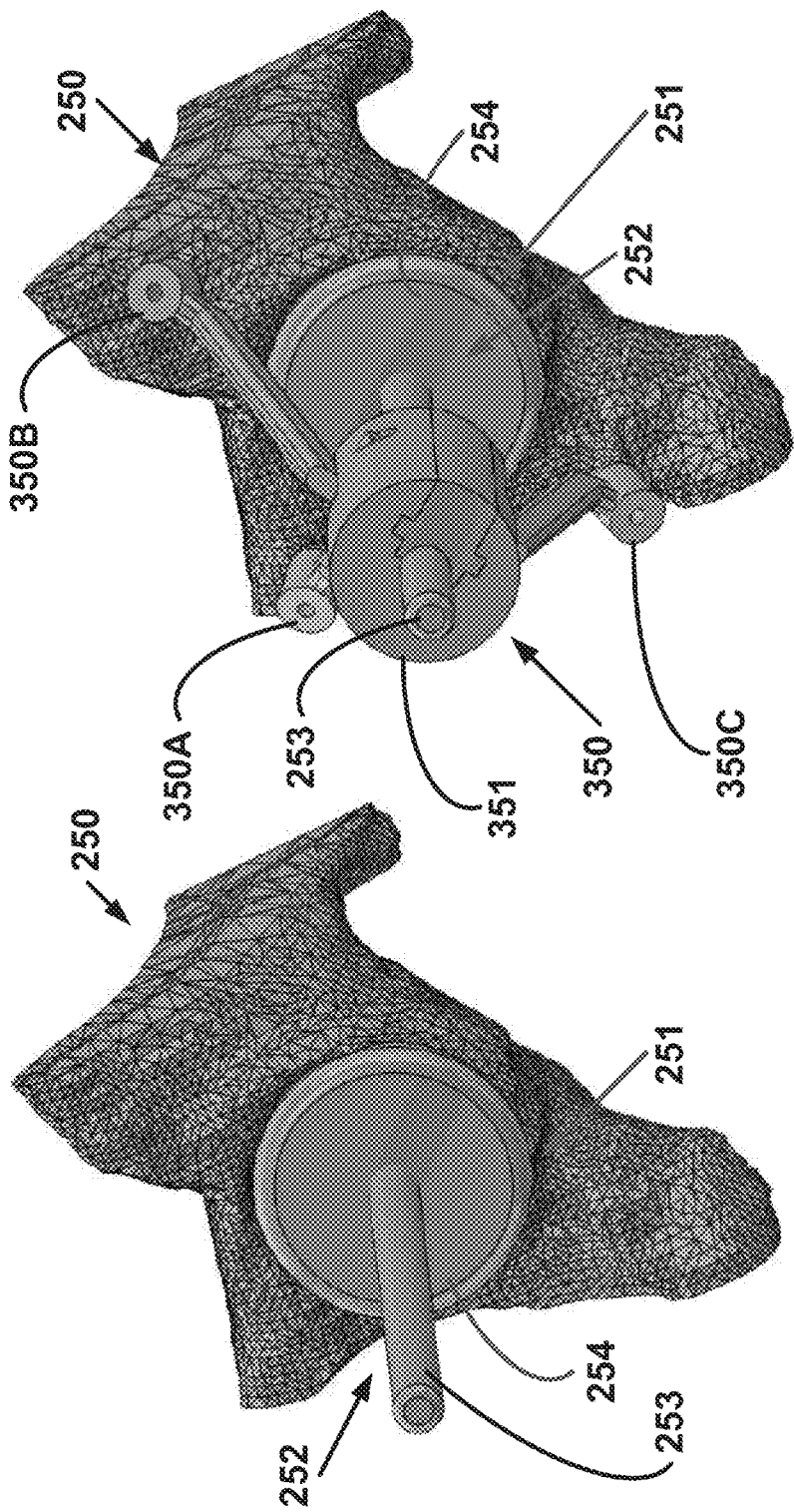
FIG. 18A-18G are views of a patient's actual hip region including the acetabular cup in the process of receiving an actual prosthetic acetabular cup via a shape-match hip guide and a silo device used in aligning the reaming of the patient's acetabular cup and/or implantation of a prosthetic acetabular cup.

A third embodiment of a method employing the guide 252 will now be discussed. FIGS. 18A and 18B are views of the patient's actual hip region 250 illustrating the process of employing a silo device 350 with the shape-match hip guide 252. In preparation for the surgical procedure, a surgeon or a surgeon's assistant will prepare the hip region of the patient for the procedure [BLOCK 285]. The preparation may include making an incision and generally preparing the patient's acetabulum to receive a prosthetic shape-match hip guide. As shown in FIG. 18A, the shape-match hip guide 252 is first matingly engaged with the patient's acetabular cup 251 as previously described herein [BLOCK 290]. As indicated in FIG. 18B, the barrel 351 of the preassembled silo 350 is slid over the rod 253 of the guide 252, and the three silo legs 350A-C extending from the silo barrel 351 are positioned for anchoring to the bone of the patient's hip region 250 [BLOCK 295].

Figures 18C, 18D:
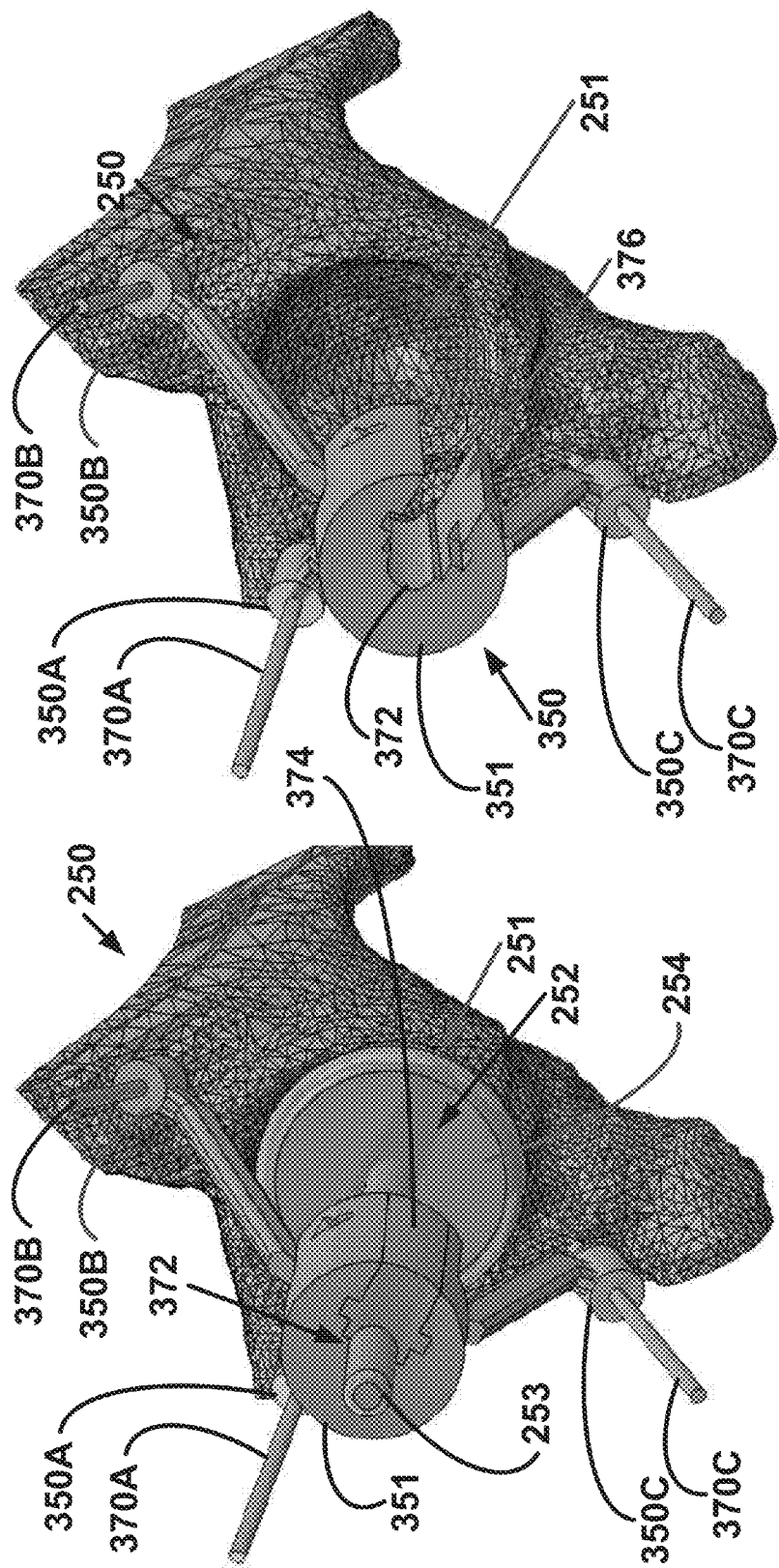

FIGS. 18C and 18D are views of the patient's actual hip region 250 further illustrating the process of employing a silo device 350 with the shape-match hip guide 252. As shown in FIG. 18C, the three silo legs 350A-C extending from the silo barrel 351 are anchored to the bone of the patient's hip region 250 via pins 370A-C, thereby securing the silo barrel guide hole 372 in the alignment of the guide rod 253 [BLOCK 295]. The barrel 351 includes a keyed side portion 374 that can be slidingly removed from the rest of the barrel 351 to reveal a side access slot 376 [BLOCK 300]. As indicated in FIG. 18D, the keyed side portion 374 has been removed from the rest of the barrel 351 to reveal the side access slot 376, and the shape-match hip guide 252 has been removed from engagement with the barrel 351 and removed from the patient's acetabular cup 251, thereby leaving the silo 350 in a fixed position properly aligned to guide an impactor. The silo device 350 may then be used to guide the reamer during the reaming of the acetabular cup 251 [BLOCK 305].

Figure 18E:
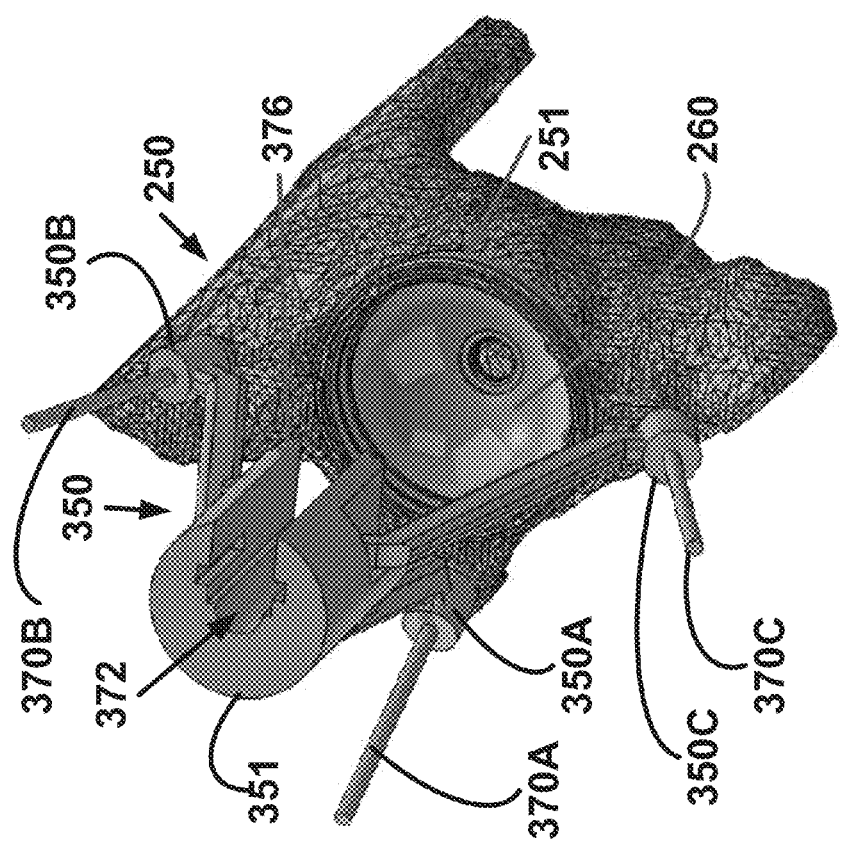
Figure 18F:
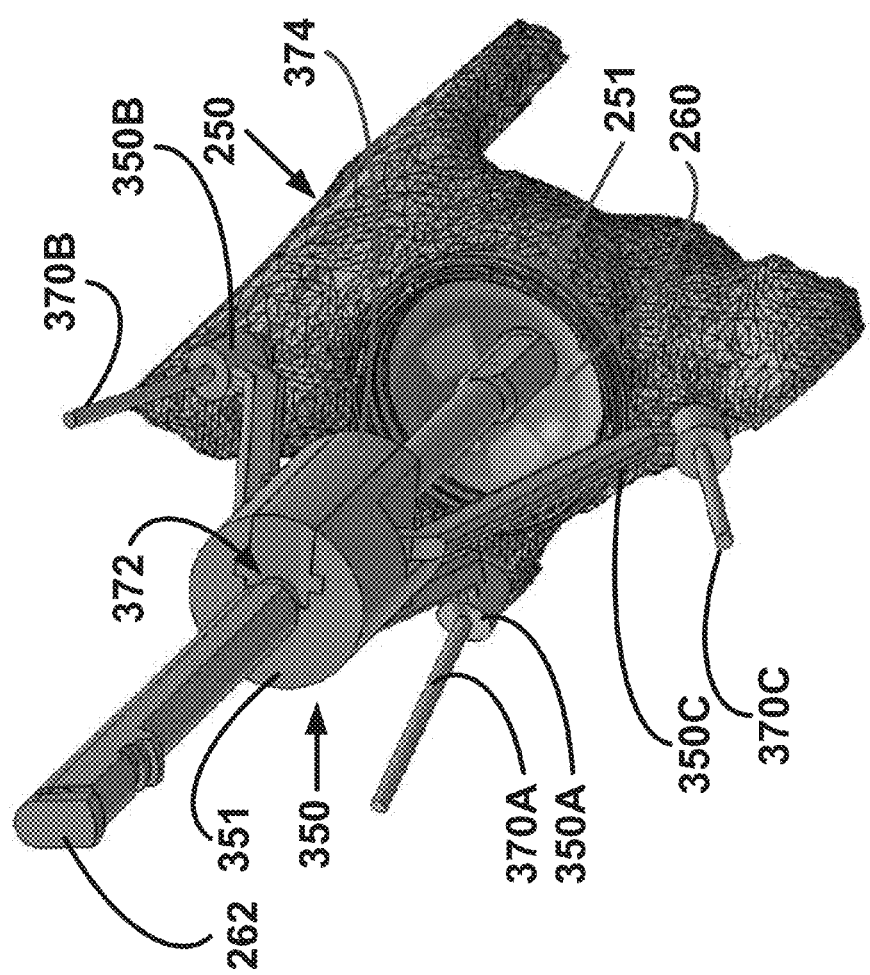
Figure 18G:
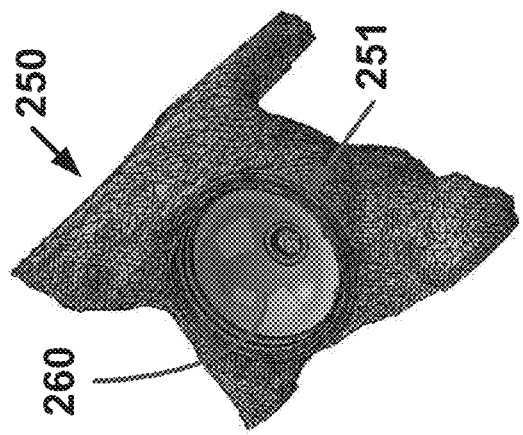

FIGS. 18E and 18F are views of the patient's actual hip region 250 further illustrating the process of employing a silo device 350 with the impactor 262. As shown in FIG. 18E, with the three silo legs 350A-C extending from the silo barrel 351 and anchored to the bone of the patient's hip region 250 via pins 370A-C, the prosthetic acetabular cup 260 is inserted into the patient's acetabular cup 251, which has already been reamed [BLOCK 315]. As illustrated in FIG. 18F, the impactor 262 enters the guide hole 372 of the silo barrel 351 via the side access slot 376 and is held in place against the prosthetic cup 260 by reinstallation of the keyed side portion 374 into the slot 376 [BLOCK 320]. As a result, the impactor 262 is held against the prosthetic cup 260 in proper alignment as established by the rod 253 of the hip guide 252 in reference to FIG. 18C. The impactor 262, which is slidingly retained in the guide hole 372, may then be impacted against the prosthetic cup 260 to seat the cup 260 in the patient's acetabular cup 251 [BLOCK 325]. As indicated in FIG. 18G, the silo 350 and impactor 262 can then be removed, leaving behind the implanted prosthetic acetabular cup [BLOCK 330].

As can be understood from a review of the three embodiments discussed with respect to FIGS. 16A-16B, 17A-17G, and 18A-18F, the embodiment of FIGS. 16A-16B may be considered a directional guide only, the embodiment of FIGS. 17A-17G may be considered a directional guide plus an outrigger device, and the embodiment of FIGS. 18A-18F may be considered a direction guide plus a silo device.

IV. Shape-Match Guide Head.

FIG. 19 illustrates three different embodiments of the custom fit mating head of the prosthetic hip guide 252 described herein. The different embodiments have the following benefits. A 50% and 33% rim overflow models make less fitment with indecisiveness. Non-overflow models make stronger and unique positioning because of the exclusion of the inaccurate anterior and posterior regions for the mating surface at the segmentation process illustrated in FIG. 8.

FIG. 20 depicts four different potential mating surface regions that may or may not be integrated into the mating surface of the head of the hip guide 252 described herein. Area A is irregular and somewhat unreliable as a mating surface. Area B is a suitable mating surface. Area C is illustrative of the fovea. Area D is considered an extra opportunity for a mating surface of the head of the hip guide.

Various modifications and additions can be made to the exemplary embodiments discussed without departing from the spirit and scope of the presently disclosed technology. For example, while the embodiments described above refer to particular features, the scope of this disclosure also includes embodiments having different combinations of features and embodiments that do not include all of the described features. Accordingly, the scope of the presently disclosed technology is intended to embrace all such alternatives, modifications, and variations together with all equivalents thereof.

What is claimed is:

1. A method of manufacturing a custom acetabular cup positioning guide for use in an arthroplasty procedure on a portion of a hip region of a patient's body, wherein the portion of the hip region includes a patient's acetabular cup, the method of manufacturing comprising:
   generating a plurality of two dimensional medical images of the portion of the hip region of the patient's body to undergo the arthroplasty procedure;
   identifying landmarks on bone boundaries in the two dimensional medical images;

identifying a hip axis line by triangulating a plurality of the landmarks in the two dimensional medical images;

using a computer processor to generate a three dimensional bone model of the portion of the hip region of the patient's body to undergo the arthroplasty procedure from the plurality of two dimensional medical images, wherein the three dimensional bone model includes a three dimensional model of the patient's acetabular cup;

shape-matching an inside surface of the three dimensional model of the patient's acetabular cup relative to the hip axis line;

generating the custom acetabular positioning guide based upon the identification of the hip axis line and a negative contour of the inside surface of the three dimensional model of the patient's acetabular cup.

2. The method of claim 1, wherein the custom positioning guide comprises a directional rod that extends generally along the hip axis line when the custom positioning guide matingly interdigitates with an inside surface of the patient's acetabular cup.

3. The method of claim 1, further comprising generating a three dimensional acetabular cup positioning guide model from the three dimensional bone model.

4. The method of claim 1, wherein the plurality of medical images are generated from MRI slices or CT slices.

5. The method of claim 1, wherein identifying landmarks on bone boundaries include a user at a user interface employing at least one of a mouse, keyboard, pen-and-tablet system, touch screen system, or spatial input device to place landmark points.

6. The method of claim 1, wherein the landmarks identified on the bone boundaries in the two dimensional images comprise a left teardrop and a right teardrop of a pelvis, a right anterior-superior ilium symphysis ("ASIS-R"), a left anterior-superior ilium symphysis ("ASIS-L"), and a pubic symphysis.

7. The method of claim 6, wherein the landmarks are identified in a coronal image slice.

8. The method of claim 6, wherein the plurality of landmarks used in triangulation in the two dimensional images include the ASIS-R, the ASIS-L, and the pubic symphysis.

9. The method of claim 8, wherein identifying the hip axis line further comprises identifying a pelvic axis line in the two dimensional images that extends through the left teardrop and the right teardrop of the pelvis.

10. The method of claim 9, further comprising determining an acute first angle between the pelvic axis line and a first line that extends through the pubic symphysis and either the ASIS-R or ASIS-L, wherein the first line will extend through the ASIS-R if a right hip region is to undergo the arthroplasty procedure and the first line will extend through the ASIS-L if a left hip region is to undergo the arthroplasty procedure.

11. The method of claim 10, further comprising identifying a second angle by increasing the first angle by a surgically prescribed degree, rotated downward from the first line, wherein the second angle is coextensive with a hip axis angle, whereby the hip axis angle is defined between the first line and the hip axis line.

12. The method of claim 11, wherein the surgically prescribed degree is about forty-five degrees.

13. A method of manufacturing a custom acetabular cup positioning guide for use in an arthroplasty procedure involving a hip region of a patient's body, wherein the hip region includes the patient's femoral head, femoral neck and acetabular cup, the guide including a mating region configured to matingly receive a portion of the patient's acetabular cup, the mating region including a surface contour that is generally a negative of a surface contour of the patient's acetabular cup, the surface contour of the mating region being configured to mate with the surface contour of the patient's acetabular cup in a generally matching or interdigitating manner when the patient's acetabular cup is matingly received by the mating region, the method of manufacture comprising:

a) generating medical imaging slices of the portion of the patient bone;

b) identifying landmarks on bone boundaries in the medical imaging slices;

c) identifying a hip axis line, the hip axis line being generally collinear with an axis of the patient's femoral head and femoral neck in a preoperative state, wherein the identifying the hip axis line comprises triangulating landmarks on the bone boundaries in the medical imaging slices;

d) using a computer processor to generate a three dimensional bone model of the patient's acetabular cup;

e) shape-matching an inner surface of the three dimensional bone model of the patient's acetabular cup relative to the bone axis line;

f) using data associated with the inner surface of the three dimensional model of the patient's acetabular cup to manufacture the custom acetabular cup positioning guide.

14. The method of claim 13, wherein the medical imaging slices are generated from MRI slices or CT slices.

15. The method of claim 14, wherein the landmarks identified on the bone boundaries in the medical imaging slices include a left teardrop and a right teardrop of a pelvis, a right anterior-superior ilium symphysis ("ASIS-R"), a left anterior-superior ilium symphysis ("ASIS-L"), and a pubic symphysis.

16. The method of claim 15, wherein the landmarks are identified in a coronal image slice.

17. The method of claim 15, wherein the landmarks used in triangulation in the two dimensional images include the ASIS-R, the ASIS-L, and the pubic symphysis.

18. The method of claim 16, wherein identifying the hip axis line further comprises identifying a pelvic axis line in the two dimensional images that extends through the left teardrop and the right teardrop of the pelvis.

19. The method of claim 18, further comprising determining an acute first angle between the pelvic axis line and a first line that extends through the pubic symphysis and either the ASIS-R or ASIS-L, wherein the first line will extend through the ASIS-R if a right hip region is to undergo the arthroplasty procedure and the first line will extend through the ASIS-L if a left hip region is to undergo the arthroplasty procedure.

20. The method of claim 19, further comprising identifying a second angle by increasing the first angle by a surgically prescribed degree, rotated downward from the first line, wherein the second angle is coextensive with a hip axis angle, whereby the hip axis angle is defined between the first line and the hip axis line.

21. The method of claim 20, wherein the surgically prescribed degree is about forty-five degrees.

* * * * *

UNITED STATES PATENT AND TRADEMARK OFFICE
CERTIFICATE OF CORRECTION

PATENT NO.         : 9,968,456 B2
APPLICATION NO.    : 15/178065
DATED              : May 15, 2018
INVENTOR(S)        : Keun Song It is certified that error appears in the above-identified patent and that said Letters Patent is hereby corrected as shown below:

In the Claims

Claim 15, Column 18, Line 34, delete "14" and replace with --13--.

Signed and Sealed this
Fourteenth Day of August, 2018

Andrei Iancu
*Director of the United States Patent and Trademark Office*